(12) United States Patent
Romo et al.

(10) Patent No.: US 10,413,437 B2
(45) Date of Patent: Sep. 17, 2019

(54) ORTHOPEDIC DEVICE HAVING A DYNAMIC CONTROL SYSTEM AND METHOD FOR USING THE SAME

(71) Applicant: Ossur Iceland ehf, Reykjavik (IS)

(72) Inventors: Harry Duane Romo, Aliso Viejo, CA (US); Jane Lee, Aliso Viejo, CA (US); Jared Olivo, Highland, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 194 days.

(21) Appl. No.: 15/016,794

(22) Filed: Feb. 5, 2016

(65) Prior Publication Data

US 2016/0151189 A1    Jun. 2, 2016

Related U.S. Application Data

(63) Continuation-in-part of application No. 14/334,152, filed on Jul. 17, 2014, which is a continuation-in-part
(Continued)

(51) Int. Cl.
*A61F 5/00* (2006.01)
*A61F 5/01* (2006.01)

(52) U.S. Cl.
CPC .......... *A61F 5/0123* (2013.01); *A61F 5/0125* (2013.01); *A61F 2005/0132* (2013.01);
(Continued)

(58) Field of Classification Search
CPC .................. A61F 5/0123; A61F 5/0125; A61F 2005/0132; A61F 2005/0165;
(Continued)

(56) References Cited

U.S. PATENT DOCUMENTS 73,768 A    1/1868 Allen
1,601,659 A    9/1926 Van Harlingen
(Continued)

FOREIGN PATENT DOCUMENTS

DE    33 20 274 A1    12/1984
DE    196 31 632 A1    2/1998
(Continued)

OTHER PUBLICATIONS

Defrate, Louis E., et al, "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.
(Continued)

*Primary Examiner* — Victoria J Hicks
(74) *Attorney, Agent, or Firm* — Workman Nydegger

(57) ABSTRACT

An orthopedic device and method for using the same are provided for applying a dynamic load on a leg of a user. The orthopedic device has a rigid or semi-rigid frame including lower and upper frames, and a hinge assembly connecting the lower and upper frames. A dynamic loading component is used to urge the load on the user's leg on the basis of flexion of the hinge assembly on the basis of tension in an elongate element connecting the dynamic loading component and at least one of the lower and upper frames. A peak load is generated at a flexion angle between extension and flexion of the hinge assembly.

9 Claims, 15 Drawing Sheets

Related U.S. Application Data of application No. 14/165,478, filed on Jan. 27, 2014, now Pat. No. 9,351,864.

(60) Provisional application No. 61/756,754, filed on Jan. 25, 2013.

(52) U.S. Cl.
CPC ............... *A61F 2005/0139* (2013.01); *A61F 2005/0165* (2013.01)

(58) Field of Classification Search
CPC ...... A61F 2005/0139; A61F 2005/0134; A61F 2005/0137; A61F 2005/0144; A61F 2005/0167; A61F 2005/0172; A61F 2005/0174; A61F 2002/075; A61F 2005/0158; A61F 2210/0004; A61F 2220/0016; A61F 2220/005; A61F 2220/0058; A61F 2220/0075; A61F 2230/0071; A61F 2250/0018; A61F 2005/0155; A61F 5/0102; A61F 5/0193; A61F 5/02; A61F 2220/0008; A61F 2250/001; A61F 5/0127
USPC ................. 602/16, 20–28; 128/882; 5/524
See application file for complete search history.

(56) References Cited

U.S. PATENT DOCUMENTS

| | | |
|---|---|---|
| 2,195,024 A | 3/1940 | Bullock |
| 2,467,907 A | 4/1949 | Peckham |
| 2,536,454 A | 1/1951 | McIntyre |
| 2,558,986 A | 7/1951 | Seelert |
| 2,959,168 A | 11/1960 | Shook |
| 3,316,900 A | 5/1967 | Young |
| 3,348,812 A | 10/1967 | Story |
| 3,444,560 A | 5/1969 | Northup, Jr. |
| 3,753,625 A | 8/1973 | Fabrizio et al. |
| 3,947,156 A | 3/1976 | Becker |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,397,308 A | 8/1983 | Hepburn |
| 4,407,276 A | 10/1983 | Bledsoe |
| 4,428,369 A | 1/1984 | Peckham et al. |
| 4,433,679 A | 2/1984 | Mauldin et al. |
| 4,463,751 A | 8/1984 | Bledsoe |
| 4,489,718 A | 12/1984 | Martin |
| 4,506,661 A | 3/1985 | Foster |
| 4,508,111 A | 4/1985 | Hepburn |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,657,000 A | 4/1987 | Hepburn |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spademan |
| 4,856,501 A | 8/1989 | Castillo et al. |
| 4,865,024 A | 9/1989 | Hensley et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A * | 3/1991 | Spademan ............ A61F 5/0125 602/16 |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,357,654 A | 10/1994 | Hsing-Chi |
| 5,437,611 A | 8/1995 | Stern |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,575,764 A | 11/1996 | Van Dyne |
| 5,588,956 A | 12/1996 | Billotti |
| 5,599,288 A | 2/1997 | Shirley et al. |
| 5,624,390 A | 4/1997 | Van Dyne |
| 5,628,722 A | 5/1997 | Solomonow et al. |
| 5,658,241 A | 8/1997 | Deharde et al. |
| 5,662,596 A | 9/1997 | Young |
| 5,683,353 A | 11/1997 | Hamersly |
| 5,685,830 A | 11/1997 | Bonutti |
| 5,807,294 A | 9/1998 | Cawley et al. |
| 5,827,208 A | 10/1998 | Mason et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Stearns et al. |
| 5,921,946 A | 7/1999 | Tillinghast et al. |
| 5,934,599 A | 8/1999 | Hammerslag |
| 5,950,245 A | 9/1999 | Binduga |
| 5,954,677 A | 9/1999 | Albrecht et al. |
| 5,997,493 A | 12/1999 | Young |
| 6,001,075 A | 12/1999 | Clemens et al. |
| 6,004,283 A | 12/1999 | Young |
| 6,074,355 A | 6/2000 | Bartlett |
| 6,110,137 A | 8/2000 | Bastyr et al. |
| 6,110,138 A | 8/2000 | Shirley |
| 6,129,690 A | 10/2000 | Hamlin et al. |
| RE37,209 E | 6/2001 | Hensley et al. |
| 6,245,034 B1 | 6/2001 | Bennett et al. |
| RE37,297 E | 7/2001 | Smith, III |
| 6,290,664 B1 | 9/2001 | Nauert |
| 6,331,169 B1 | 12/2001 | Bastyr et al. |
| 6,409,693 B1 | 6/2002 | Brannigan |
| 6,413,232 B1 | 7/2002 | Townsend et al. |
| 6,425,166 B1 | 7/2002 | Seligman et al. |
| 6,436,058 B1 | 8/2002 | Krahner et al. |
| 6,471,664 B1 | 10/2002 | Campbell et al. |
| 6,500,138 B1 * | 12/2002 | Irby ............ A61F 5/0125 602/26 |
| 6,551,264 B1 | 4/2003 | Cawley et al. |
| 6,666,837 B2 | 12/2003 | Weihermuller |
| 6,740,054 B2 | 5/2004 | Stearns |
| 6,752,775 B2 | 6/2004 | Seligman et al. |
| 6,834,752 B2 * | 12/2004 | Irby ............ A61F 5/0125 192/26 |
| 6,875,187 B2 | 4/2005 | Castillo |
| 6,936,020 B2 | 8/2005 | Davis |
| 6,993,808 B1 | 2/2006 | Bennett et al. |
| 7,004,919 B2 | 2/2006 | Gaylord et al. |

(56) References Cited

U.S. PATENT DOCUMENTS

| | | |
|---|---|---|
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,960 B2 | 4/2007 | Kenney |
| 7,235,058 B2 | 6/2007 | Doty et al. |
| 7,235,059 B2 | 6/2007 | Mason et al. |
| 7,309,322 B2 | 12/2007 | Albrecht et al. |
| 7,311,687 B2 | 12/2007 | Hoffmeier et al. |
| D577,828 S | 9/2008 | Ingimundarson et al. |
| 7,431,708 B2 | 10/2008 | Sreeramagiri |
| 7,435,234 B2 | 10/2008 | Gamada |
| 7,485,103 B2 | 2/2009 | Mason et al. |
| 7,500,957 B2 | 3/2009 | Bledsoe |
| 7,534,217 B2 | 5/2009 | Seligman et al. |
| 7,534,219 B2 | 5/2009 | Stearns |
| 7,544,174 B2 | 6/2009 | Nathanson |
| 7,553,289 B2 | 6/2009 | Cadichon |
| 7,597,675 B2 | 10/2009 | Ingimundarson et al. |
| 7,662,122 B2 | 2/2010 | Sterling |
| 7,722,555 B2 | 5/2010 | Doty et al. |
| 7,727,174 B2 | 6/2010 | Chang et al. |
| 7,749,183 B2 | 7/2010 | Ingimundarson et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,927,299 B2 | 4/2011 | Krause |
| 7,963,933 B2 | 6/2011 | Nace |
| 8,048,013 B2 | 11/2011 | Ingimundarson et al. |
| 8,128,587 B2 | 3/2012 | Stevenson et al. |
| 8,376,974 B2 | 2/2013 | Nace |
| 8,882,688 B1 | 11/2014 | Ancinec |
| 8,920,350 B2 | 12/2014 | Merkley et al. |
| 9,220,624 B2 | 12/2015 | Jansson et al. |
| 2002/0013544 A1 | 1/2002 | Stearns |
| 2002/0052568 A1 | 5/2002 | Houser et al. |
| 2002/0052663 A1 | 5/2002 | Herr et al. |
| 2002/0133108 A1 | 9/2002 | Jagodzinski |
| 2004/0002674 A1 | 1/2004 | Sterling |
| 2004/0030411 A1 | 2/2004 | Caspers |
| 2004/0049140 A1 | 3/2004 | Doty et al. |
| 2004/0049290 A1 | 3/2004 | Bedard |
| 2004/0054307 A1 | 3/2004 | Mason et al. |
| 2004/0054311 A1 | 3/2004 | Sterling |
| 2004/0068215 A1 | 4/2004 | Adelson et al. |
| 2004/0097859 A1 | 5/2004 | Stearns |
| 2005/0015156 A1 | 1/2005 | Hikichi |
| 2005/0020951 A1 | 1/2005 | Gaylord et al. |
| 2005/0177082 A1 | 8/2005 | Bledsoe |
| 2005/0245853 A1 | 11/2005 | Scorvo |
| 2005/0273025 A1 | 12/2005 | Houser |
| 2006/0100560 A1 | 5/2006 | Gilmour |
| 2006/0100561 A1 | 5/2006 | Gilmour |
| 2006/0116616 A1 | 6/2006 | Albrecht et al. |
| 2006/0135902 A1 | 6/2006 | Ingimundarson et al. |
| 2006/0142680 A1 | 6/2006 | Iarocci |
| 2007/0010772 A1 | 1/2007 | Ryan |
| 2007/0050044 A1 | 3/2007 | Haynes et al. |
| 2007/0100265 A1 | 5/2007 | Gamada |
| 2007/0232972 A1 | 10/2007 | Martinez |
| 2007/0270976 A1 | 11/2007 | DeHarde et al. |
| 2008/0051684 A1 | 2/2008 | Gamada |
| 2008/0066272 A1 | 3/2008 | Hammerslag et al. |
| 2008/0195013 A1 | 8/2008 | Ingimundarson et al. |
| 2008/0200856 A1 | 8/2008 | Cadichon |
| 2008/0249448 A1 | 10/2008 | Stevenson et al. |
| 2008/0294079 A1 | 11/2008 | Sterling et al. |
| 2009/0054819 A1 | 2/2009 | Einarsson |
| 2009/0076426 A1 | 3/2009 | Einarsson et al. |
| 2009/0099495 A1 | 4/2009 | Campos et al. |
| 2009/0099562 A1 | 4/2009 | Ingimudarson et al. |
| 2009/0105622 A1 | 4/2009 | Sterling et al. |
| 2009/0124948 A1 | 5/2009 | Ingimundarson et al. |
| 2009/0171469 A1 | 7/2009 | Thorsteinsson et al. |
| 2009/0240181 A1 | 9/2009 | Sreeramagiri et al. |
| 2009/0259154 A1 | 10/2009 | Nace |
| 2009/0281637 A1 | 11/2009 | Martin |
| 2009/0287128 A1 | 11/2009 | Ingimundarson et al. |
| 2010/0010409 A1 | 1/2010 | Bejarano |
| 2010/0056970 A1 | 3/2010 | Nace |
| 2010/0162539 A1 | 7/2010 | Rancon |
| 2011/0098618 A1 | 4/2011 | Fleming |
| 2011/0270413 A1 | 11/2011 | Haynes |
| 2012/0022667 A1 | 1/2012 | Accinni et al. |
| 2012/0046585 A1 | 2/2012 | Lee et al. |
| 2012/0059296 A1 | 3/2012 | Kompa |
| 2012/0157902 A1 | 6/2012 | Castillo et al. |
| 2013/0110020 A1 | 5/2013 | Ingimundarson et al. |
| 2013/0150761 A1 | 6/2013 | Romo et al. |
| 2013/0172797 A1* | 7/2013 | Merkley ............... A61F 5/0102 602/16 |
| 2013/0178771 A1 | 7/2013 | Moir et al. |
| 2013/0331754 A1 | 12/2013 | Dunn et al. |
| 2014/0213948 A1 | 7/2014 | Romo et al. |
| 2015/0005685 A1 | 1/2015 | Chetlapalli et al. |
| 2016/0120683 A1 | 5/2016 | Romo et al. |

FOREIGN PATENT DOCUMENTS

| | | |
|---|---|---|
| DE | 196 45 076 A1 | 5/1998 |
| DE | 198 11 925 A1 | 10/1999 |
| DE | 10 259 751 A1 | 7/2004 |
| DE | 10 2010 006 089 A1 | 8/2010 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| WO | 86/04228 A1 | 7/1986 |
| WO | 9522700 A1 | 8/1995 |
| WO | 95/27451 A1 | 10/1995 |
| WO | 96/16615 A1 | 6/1996 |
| WO | 2004/056293 A1 | 7/2004 |
| WO | 2006/044423 A2 | 4/2006 |
| WO | 2009126724 A2 | 10/2009 |
| WO | 2010/087899 A2 | 8/2010 |

OTHER PUBLICATIONS

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded, 1 page.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", The American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom & OTS Knee Brace, "Application Instructions & Patient Manual: Instructions for ACL or PCL

(56) References Cited

OTHER PUBLICATIONS

Symptoms", Jan. 2007, pp. 1-4 vol. CP020223, Rev B, Publisher: Bledsoe Brace Systems, Published in: US. http://www.bledsoebrace.com/pdf/Al/Axiom-Al.pdf.
Brochure: Armor Fourcepoint, Donjoy Product pages http://www.donjoy.com/armorfp. Downloaded, Oct. 2011, 2 pages. Published: US.
Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.
Brochure: "Fusion XT OA", Bregg 360 Customer Care, Product page http://www.breg.com/knee-bracing/oa/fusion-xt-oa.html, downloaded, Oct. 2011, 2 pages. Publisher Orthofix, Published in: US.
Brochure: "CTI Custom", OSSUR Product page from http://www.ossur.com/?PageID=13230 downloaded, Oct. 2011, 2 pages. Publisher: Ossur Americas, Published in: US.
Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.
International Search Report and Written Opinion regarding Application No. PCT/US2011/051627, Jan. 6, 2012.
International Search Report from corresponding PCT Application No. PCT/US2012/062702, Feb. 15, 2013.
International Preliminary Report on Patentability regarding Application No. PCT/US2011/051627, Mar. 28, 2013.
Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf, 37 pages.
Extended European Search Report from EP Application No. 12150517.6, May 22, 2012.
Smith, Sean D. et al., "Functional bracing of ACL injuries: current state and future directions", Knee Surgery Sports Traumatology Arthhroscopy, Springer, Apr. 27, 2013, 11 pages.
Knapik, Joseph J. et al., Isometric, Isotonic and Isokinetic Torque Variations in Four Muscle Groups Through a Range of Joint Motion, "Physical Therapy: Journal of the American Physical Therapy Association and de Fysiotherapeut", 1983, vol. 63, No. 6, pp. 938-947, downloaded from http://ptjournal.apta.org/ on Apr. 15, 2014.
International Search Report and Written Opinion from International Application No. PCT/US2014/013245, May 6, 2014.
Jansson, Kyle S. et al., "A Historical Perspective of PCL Bracing", Knee Surgery Sports Traumatology Arthhroscopy, Springer-Verlag, May 24, 2012, 7 pages.
International Search Report from corresponding International Application No. PCT/US2014/042989, Oct. 15, 2014.

* cited by examiner

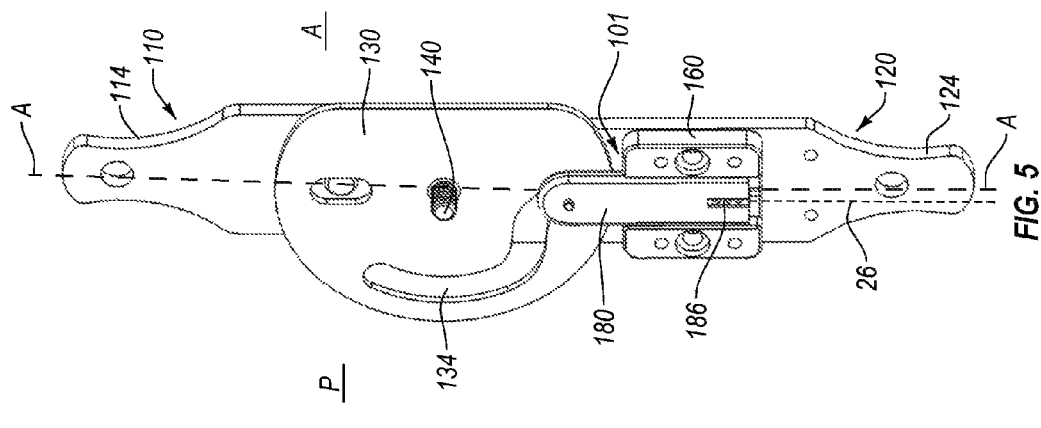
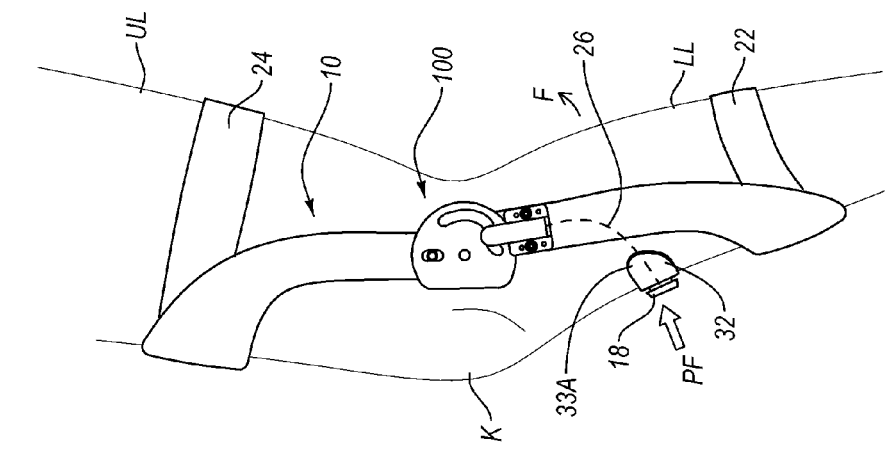
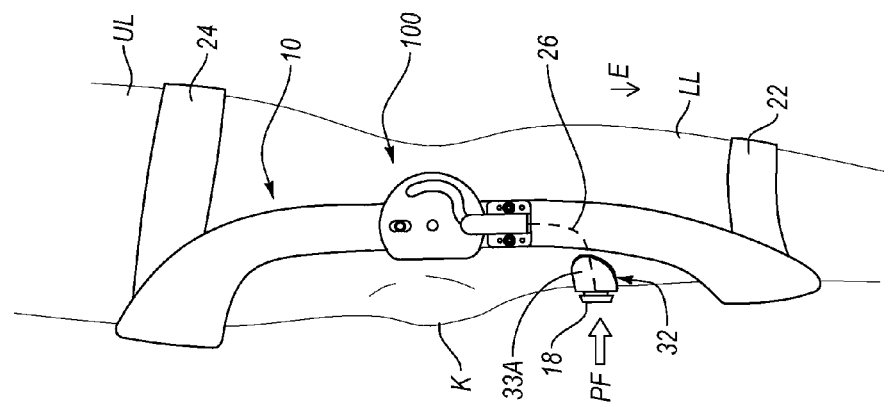

ORTHOPEDIC DEVICE HAVING A DYNAMIC CONTROL SYSTEM AND METHOD FOR USING THE SAME

FIELD OF THE DISCLOSURE

This disclosure relates to an orthopedic device having a dynamic control system for providing variable assistance during gait, particularly as a user flexes a knee, and a method generally providing increased loading at certain flexion angles and diminished loading at other flexion angles and extension.

BACKGROUND

There are roughly 200,000 partial or complete anterior cruciate ligament ("ACL") injuries per year in the U.S. The ACL is an intracapsular ligament that cannot spontaneously heal complete tears. Approximately 50% (100,000 U.S. patients) of ACL injuries go untreated either through a lack of diagnosis or repair is deemed unnecessary due to the patient's low level of activity.

Partial ACL tears may heal spontaneously but may heal at an increased length resulting in a positive "Drawer Test" (a commonly used test to detect the rupture of cruciate ligaments in the knee) and the ability of the tibia to shift anteriorly regarding the femur. In the Drawer Test, if the tibia pulls forward or backward more than normal, the test is positive. Excessive displacement of the tibia anteriorly indicates the ACL is likely torn, whereas excessive posterior displacement of the tibia indicates the PCL is likely torn. Complete ACL tears that go unrepaired will cause a positive Drawer Test.

Some surgeons show positive results in healing for some patients with ACL injury through minor surgical intervention by reattaching the ACL.

For the remaining 100,000 patients who undergo ACL repair for complete tears, some studies have shown the strength of the ACL ligament is reduced to approximately 50% of its original strength 6 months after surgery. This may be due to the revascularization of the ACL ligament. At six months, these patients often feel stable enough to return to their previous level of activity. This places the ACL at risk because the patient does not realize the ACL is only at 50% of its original strength.

During normal activity, tension on the ACL may vary. Activities that require sudden stops and changes of direction may place high tension on the ACL or create displacement of the tibia regarding the femur. Adjustment of the tibia relative to the femur, and possibly reduction of ACL tension could benefit the patient in the following ways: (1) reduce additional injury and preserve the length of the partially torn ACL, and (2) reduce the risk of reinjury of the graft for the ACL repaired patient.

SUMMARY

According to various exemplary orthopedic device embodiments of the disclosure, an orthopedic device may take the form of a knee brace preferably providing a dynamic posteriorly directed force on the anterior tibia or dynamic anteriorly directed force on the posterior femur. The brace has a rigid or semi-rigid frame including lower and upper frames, and a hinge assembly that connects the lower and upper components.

With the embodiments, loading on the leg, whether the femur or tibia, and on either posterior or anterior sides, is generally achieved at increased amounts depending on predetermined angles and diminished amounts outside the predetermined angles. The reduced loading outside the predetermined angles is preferably gradual, and is achieved by means of interacting with a hinge articulating from extension to flexion and vice versa.

A dynamic loading component, such as a femoral or tibial shell, is used to alter the femur relative to the tibia with an adjustment device. According to an embodiment, the dynamic loading component may be flexible relative to the brace frame and is connected to the lower component to move posteriorly toward a user's tibia, particularly in relationship to the lower component. A variable clearance is defined between the tibial shell and the lower frame. An adjustment device is arranged for regulating the degree to which the tibial shell is initially drawn to the anterior tibia. The adjustment device has an elongate element that connects the tibial shell to the hinge. The tibial shell may be moved toward the lower frame by reducing a width of the variable clearance. The adjustment device couples to the hinge assembly such that the tibial shell is urged inwardly toward the lower frame as the knee undergoes flexion and extension from articulation of the hinge assembly.

In a variation, the dynamic loading component may be rigid or semi-rigid, and is not limited to being flexible. The dynamic loading component, although described above as moving the tibia, may be placed above the hinge and on the posterior side of the orthopedic device so as to connect to the upper frame.

The elongate element secures to the hinge to encourage greater tension in the elongate element as the brace is flexed and extended. The adjustment device may have first and second elongate elements each extending from first and second sides, respectively, of the adjustment. The adjustment device may be adapted for simultaneously regulating the length of the first and second elongate elements. The elongate element may extend laterally from the adjustment device to at least one of the lateral or medial sides of the lower frame. A guide element may be arranged to longitudinally route the at least one elongate element along the lower frame toward the hinge assembly.

The orthopedic device may include a cam assembly coupling to the hinge assembly. In an embodiment, the cam assembly includes a cam plate and a cam follower for engaging the cam plate connected to a lower strut belonging to the lower frame. The at least one elongate element connecting to the cam follower enables a variable force to be exerted by the tibial shell on the basis of travel of the cam follower and tension created in the at least one elongate element due to resistance against a user's tibia by the tibial shell. The cam assembly can be arranged on the upper strut should the dynamic loading component be placed on the upper, posterior side of the orthopedic device.

The cam plate may define an eccentric shape including at least two segments arranged in different directions: a first segment extending generally linearly and the second segment extending generally arcuately. The cam plate may define an eccentric shape arranged to urge the tibial or femoral shell toward the lower or upper frame at a greatest force between 10 to 40 degrees flexion of the hinge assembly by reducing the variable clearance and/or creating tension in the elongate element. The cam assembly may be urged at an increasing force to a maximum force within the range of 10 to 40 degrees of flexion of the hinge assembly.

A guide block may be secured to the lower strut and the cam follower may be arranged to slidably engage the guide block depending on the relationship of the cam follower to the cam plate. The cam follower may include a piston arranged to slide longitudinally within a slot defined by the guide block.

The hinge assembly may be provided by itself for attachment to an orthopedic device and include a first strut, a second strut pivotally connected to the first strut, and a cam assembly including a cam plate having a guide slot with a certain shape and pivotally attached to one of the first and second struts, and a cam follower adapted to engage the guide slot to travel along the guide slot shape. A block may be arranged on one of the first and second struts and adapted to receive the cam follower arranged to piston within the block. The hinge assembly may alternatively have the features described with the hinge assembly and cam assembly of the orthopedic device embodiments.

A method provides variable assistance during gait and may include the steps of providing any of the embodiments and variations of the orthopedic device on a leg of a user with the orthopedic device having a shell adapted to apply pressure against a lower leg of a user. The method involves urging a posteriorly directed force against an anterior tibia of a user during an initial stage of flexion of a leg. The method may yet further include diminishing the posteriorly directed force after the initial stage of flexion. The method may also include initially setting a predefined load at a predetermined angle of flexion before a user's knee undergoes range of motion.

As correlated with experimental data, the method for applying a dynamic load on a user's leg during flexion of a knee involves approximating an exemplary ACL tension curve by placing an orthopedic device having a hinge assembly on a leg of a user, urging a load on a user's leg by the orthopedic device, and creating a peak load on the leg corresponding to a predetermined angle of flexion of the hinge assembly. The method may include increasing the load from full extension to the peak load at the predetermined angle of flexion, and diminishing the load after reaching the predetermined angle of flexion as the leg continues to undergo flexion. The load at full extension may be greater than the load at full flexion The load exerted on the user's leg defines a generally concave curve from full extension through the predetermined angle of flexion and a particular angle of flexion greater than the predetermined angle of flexion, and a generally convex curve after the particular angle of flexion to full flexion unlike an exemplary ACL tension curve.

The load may be dynamic by a cable regulating the load on the basis of articulation of the hinge assembly and having at least one end secured to the hinge assembly. The peak load may occur when the cable intersects the instantaneous center of rotation of the hinge assembly. A minimum load may occur when the cable has a shortest length. The cable may have a maximum length at the peak load.

The orthopedic device may include a dynamic loading component arranged to be urged against a user's leg. The cable may have a first end securing to the dynamic loading component and a second end securing to the hinge assembly. The hinge assembly may include a hinge and the first end of the cable is located on a first side of the hinge and the second end of the cable is located on a second side of the hinge such that the cable sweeps over the hinge during articulation of the hinge. The initial load may be set by regulating the dynamic loading component before a user's knee undergoes extension or at another designated flexion angle.

The method includes applying a first force on a first side of the leg above the user's knee, and applying a second force on the first side of the leg below the user's knee. The load may be applied on a second side of the leg, and the load counteracts in a second direction the first and second forces, which are directed in a first direction opposite the second direction.

The tibial shell may apply a greater posteriorly directed force against an anterior tibia of a user during the initial stage of flexion of the leg and during the final stage of extension of the leg. As force applies to the anterior tibia, anterior tibia shift regarding the femur is neutralized or minimized due to the posterior force. As the leg continues to be extended after the initial stage of flexion, the posteriorly directed force increases up to a peak load and then diminishes after peak load to full extension (0 degrees flexion). The initial tension in the elongate element may be set by a clinician based on a user's individual load requirement, and the adjustment device may be temporarily locked after the initial load is set.

The dynamic loading component can be arranged posteriorly above the knee so it is arranged on the distal posterior thigh of a user so as not to impinge on a user's popliteal. In this embodiment, posterior dynamic compression from the dynamic loading component urges the femur anterior relative to the tibia similar to the manner in which the tibial shell urges the posterior relative to the femur, and produces the same dynamic load to assist users with impaired knee ligaments.

In a variation, the uprights may include a cutout to urge a load more in a saggital plane rather than a coronal place. This enables a cable to extend more saggitally and more loading of the posterior femur anteriorly or loading of the anterior tibia posteriorly. It has been found that medial collateral ligament injuries are often concurrent with ACL injuries and therefore reduction of the coronal (medial/lateral directions) pressure minimizes contact pressure on such surgical regions.

Various hinge assemblies may include a cam assembly having a cam surface and cam follower connected to the hinge assembly and arranged to create peak tension at a predetermined angle generating tension in the cable. Routing parts can reduce slack in the cable and maintain tension and remain at cable tension during flexion to extension.

The numerous other advantages, features and functions of embodiments of an orthopedic device will become readily apparent and better understood in view of the following description and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of an orthopedic device according to the present disclosure.

FIG. 3 is a schematic side elevational view showing the orthopedic device according to FIG. 1 on a leg in a fully extended position.

FIG. 4 is a schematic side elevational view showing the orthopedic device according to FIG. 1 on a leg during an initial stage of flexion.

FIG. 5 is a perspective view of a hinge assembly according to the embodiment of FIG. 1.

DETAILED DESCRIPTION OF VARIOUS EMBODIMENTS

A. Overview

Figure 1:
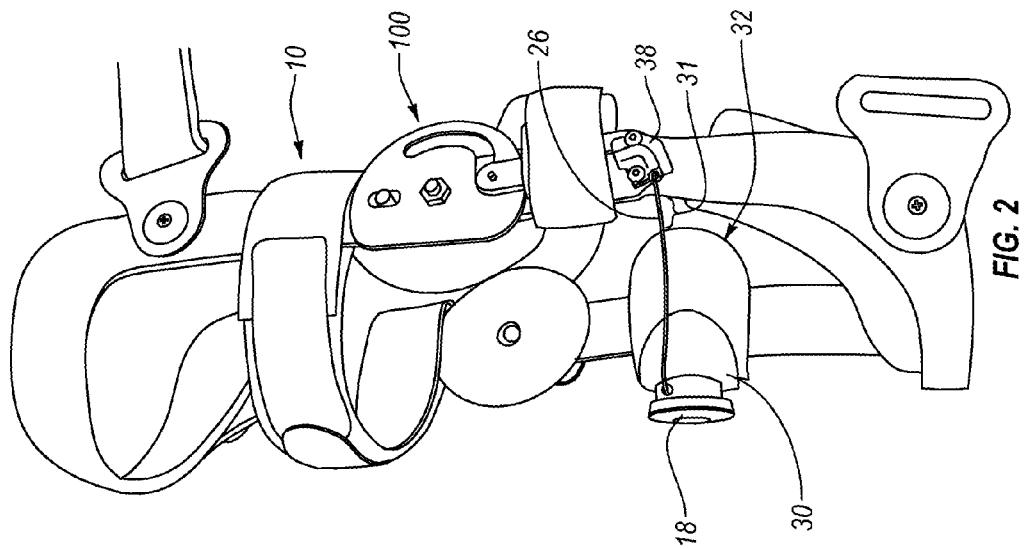
FIG. 1 is a front elevational view showing a first embodiment of an orthopedic device having a dynamic control system.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning.

Any element in a claim that does not explicitly state "means for" performing a specified function, or "step for" performing a function is not to be interpreted as a "means" or "step" clause as specified in 35 U.S.C. §112, paragraph 6.

B. Definitions

For ease of understanding the disclosed embodiments of an orthopedic device, the anterior and posterior portions of the orthopedic device may be described independently. Anterior and posterior portions of the orthopedic device function together to support and stabilize anatomical portions of the user of the device.

For further ease of understanding the embodiments of an orthopedic device as disclosed, a description of a few terms, when used, is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid" and "flexible" may distinguish characteristics of portions of certain features of the orthopedic device. The term "rigid" should denote an element of the device is generally devoid of flexibility. Within the context of frame or support members or shells that are "rigid," it should indicate that they do not lose their overall shape when force is applied, and they may break if bent with sufficient force. The term "flexible" should denote that features are capable of repeated bending such that the features may be bent into retained shapes or the features do not retain a general shape, but continuously deform when force is applied.

As for the term "semi-rigid," this term is used to connote properties of support members or shells that provide support and are free-standing; however such support members or shells may have some degree of flexibility or resiliency.

C. Various Embodiments of the Orthopedic Device

Figure 2:
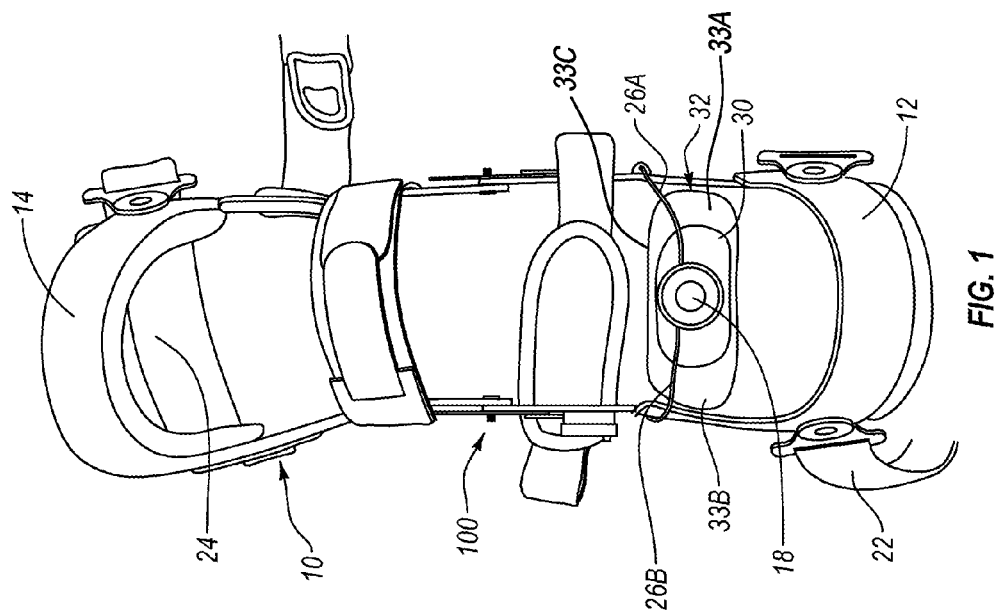
FIG. 2 is a side elevational view showing the embodiment of FIG. 1.

According to an embodiment illustrated in FIGS. 1 and 2, the orthopedic device is a knee brace including a dynamic load control system. The dynamic load control system has a hinge assembly or adjustment device 100 configured for attachment to lower and upper components 12, 14 for securing the brace onto a user's leg below and above the knee, respectively. The hinge assembly 100 advantageously provides dynamic force adjustment to the knee brace 10, especially in neutralizing undesired forces on a patient's ACL in the anterior and posterior directions.

The knee brace 10 has a rigid or semi-rigid frame including the lower and upper components 12, 14 preferably but not limited to being connected to one another by the hinge assembly 100 on both the medial and lateral sides of the brace. Lower and upper straps 22, 24 may extend from the lower and upper components 12, 14 for securing the brace onto a user's leg below and above the knee, respectively. The knee brace frame may take on many shapes, such as those shown and described in U.S. Pat. No. 5,230,697, granted Jul. 27, 1993, U.S. Pat. No. 8,048,013, granted on Nov. 1, 2011, and U.S. patent application publication 2012/

0046585, published on Feb. 23, 2012, each of which are incorporated by reference in their entirety.

According to the device, a dynamic loading component is movably connected to the lower component 12. In this embodiment, the dynamic loading component is preferably a tibial shell 32; however the dynamic loading component can be rearranged as a femoral shell for loading the femur rather than the tibia. The tibial shell 32 preferably includes first and second wings 33A, 33B adapted to yield in part over a tibia of a user. The tibial shell 32 also includes a central portion 33C from which the first and second wings 33A, 33B extend.

An adjustment device 18 is mounted on the tibial shell 32 preferably at the central portion 33C by a plate 30 arranged to stably secure the adjustment device 18 on the subshell 32. The adjustment device 18 includes one or more elongate elements 26A, 26B and is regulated by the length of a segment of the elongate elements 26A, 26B extending from the adjustment device 18. It should be appreciated, however, that the adjustment device may alternatively be secured elsewhere on the brace.

The adjustment device 18 regulates the length of one or more elongate elements 26A, 26B between the adjustment device 18 and the lower frame 12, and moves or attempts to move the tibial shell toward the lower frame 12 by reducing a width of a variable clearance 31 between one of the first and second wings 33A, 33B, and the lower frame 12. In a variation, the clearance does not modify or adjust during movement of the hinge assembly from extension to flexion, but the distance or tension of the at least one elongate element is maintained or increased as the hinge assembly moves, to maintain or increase pressure or force exerted on the tibia by the tibial shell depending on the position position of flexion.

The adjustment device may be a dial tensioning device provided by BOA Technology Inc., or an adjustment device described in U.S. Pat. No. 7,198,610, granted Apr. 7, 2007, and U.S. patent application publication no. 2009/0287128, published Nov. 19, 2009, which are incorporated by reference and belong to the assignee of this disclosure.

The tibial shell 32 is secured to the lower component 12 by anchors 38 (FIG. 2) securing the elongate elements 26 to the brace. The elongate elements 26 tether the tibial shell 32 to the lower component 12 while permitting movement of the tibial shell relative to the lower component. Suitable padding may also be provided along various portions of the knee brace including along the lower and upper components, and the subshell.

As with any other embodiments described, the adjustment device 18 may include indicia that allow for an understanding of relative configuration as the adjustment device is regulated. The clinician may initially set the adjustment device, and the adjustment may be locked to provide consistent dynamic adjustment over extension and flexion. Alternatively, the user may regulate the adjustment device as needed.

In this embodiment, two segments of the elongate element 26A, 26B extend from opposed sides, such as lateral and medial sides, of the adjustment device 18. The segments 26A, 26B extend along the lower component 12 and may be aided by guides located thereon. The anchors 38 may also help guide the segments 26A, 26B along the brace in the direction toward the hinge 100. The segments 26A, 26B are additionally secured to the hinge assembly 100, as will later be discussed. While the path of the segments 26A, 26B along the lower component to the hinge is in a symmetrical configuration on the lateral and medial sides of the brace, it will be understood that the segments 26A, 26B may be arranged in different paths relative to one another in variations of the brace. The elongate element may be a cable, lace or other suitable elongate element and these terms are used interchangeably with one another for an element that can be regulated in length extending from the adjustment device.

FIG. 3 shows the knee K in full extension E (0 degrees flexion), whereby the upper leg UL and the lower leg LL are in a generally straight configuration. When in extension, the tibial shell 32 exerts a posteriorly directed force PF against the anterior tibia to urge the tibia posteriorly, particularly since the elongate element 26 is taut in view of the relative position of the lower component relative to the upper component and biased by the hinge 100. The tibial shell assists an injured ACL by preventing the tibia from advancing anteriorly when the knee is in extension E.

FIG. 4 shows the knee K in an initial stage of flexion F, whereby the lower leg LL and upper leg UL are arranged at an angle relative to one another such that the knee K is bent. The arrangement of the hinge 100 causes tension in the elongate element 26 to increase during the initial stage of flexion, and then return to its original tension level as the knee continues to be flexed. This way the posterior force PF is substantially more when the knee is initially flexed as opposed to when the knee is fully extended.

As illustrated in FIGS. 5-9, an embodiment of the hinge assembly 100 comprises a rigid frame including an upper strut 110 having an upper pivot end 112 and an upper support end 114, and a lower strut 120 having a lower pivot end 122 and a lower support end 124. In a preferred embodiment the upper and lower struts are substantially flat; however, they may have other shapes such as curved to anatomically accommodate a user's leg and/or movement. The upper and lower struts are pivotally connected at each respective pivot end by a first pivot member 116 defining a hole formed on the upper strut for pivotally engaging a second pivot member 126 defining a corresponding protrusion formed on the lower strut. The first pivot member 116 may be shaped to pivotally receive the second pivot member 126 such that each strut maintains a low profile when connected.

The upper support end 114 of the upper strut 110 is configured for attachment to the upper component 14 of the brace, and the lower support end 124 of the lower strut 120 is configured for attachment to the lower component 12 of the brace.

The hinge assembly 100 further comprises a cam assembly 101 including a cam plate 130 pivotally attached at a pivot portion 132 to the lower pivot end 122 of the lower strut 120 by a fastening member 140. In a preferred embodiment the cam plate is generally flat, although it may be curved or arranged in other forms to accommodate movement of a knee. The fastening member is preferably configured to fixedly secure the cam plate 130 to the upper pivot end 112 of the upper strut, so the lower strut 120 may pivot about both the cam plate 130 and the upper strut 110 at the lower pivot end 122. The fastening member may include a bolt having a partially threaded shank.

It will be understood the hinge assembly 100 is not limited to the single axis hinge structure depicted and discussed for coupling the upper and lower struts 110, 120. A wide variety of types of hinges may couple the upper and lower struts, including but not limited to four-bar hinges of the type described in U.S. patent application publication nos. 2012/0059296, published on Mar. 8, 2012, 2013/0331754, published on Dec. 12, 2013, incorporated by their entirety, polycentric hinges of the type described in U.S. patent application publication nos. 2004/0002674, published on Jan. 1, 2004 incorporated by its entirety, and U.S. Pat. No. 7,198,610, and other types of known hinges used in the art of knee bracing.

The lower pivot end 122 of the lower strut 120 further defines a through-hole 128 axially extending through both the second pivot member 126 and the lower strut, and which is adapted to receive the fastening member 140. An accompanying retaining member 150, such as a washer, may help retain the fastening member to the upper strut 110. This allows the fastening member to fixedly secure the upper strut 110 to the cam plate 130, with the lower strut 120 pivotally coupled between both the upper strut and the cam plate.

A guide block 160 having a substantially flat first surface 162 is fixedly secured to an intermediate portion 123 of the lower strut 120 and located adjacent to the cam plate 130. A second surface 164 on a side of the guide block 160 opposed to the first surface 162 defines a longitudinal groove or slot 166 for movably connecting to and guiding a first end 182 of a piston 180 to permit longitudinal movement B. A second end 184 of the piston 180 is configured to extend beyond the guide block 160 in a direction toward the pivot portion 132 of the cam plate 130 and is fixedly secured to a guide member 190.

The guide member 190 is retained within an eccentric guide slot 134 formed on the cam plate 130 and is adapted to move toward the guide slot. The combination of the piston 180 and the guide member 190 affixed thereto form a cam follower 170. The guide member 190 correspondingly moves within the guide slot 134 as the lower strut 120 is pivotally rotated relative to both the upper strut 110 and the cam plate 130 urging the piston 180 either toward or away from the pivot portion 132 of the cam plate as it follows the eccentric shape of the guide slot.

Preferably, the eccentric shape of the guide slot 134 is configured such that when the guide member 190 reaches a first end 136, the upper and lower struts 110, 120 are longitudinally aligned for supporting the brace in a fully extended position. Conversely, when the guide member 190 engages a second end 138 of the guide slot 134, the upper and lower struts 110, 120 are pivotally positioned relative to each other for supporting the brace in a fully flexed position. The cam follower 170 may also act as a pivot limiter by preventing the lower strut from pivoting relative to both the upper strut and the cam plate beyond a set position in either extension or flexion.

The eccentric guide slot 134 provides dynamic control to the force applied to the user's tibia in the posterior direction. The shape of the guide slot is further configured such that the cam follower 170 is briefly urged from an original, or neutral, position toward the pivot portion 132 of the cam plate 130 during the initial stage of flexion of a patient's knee, and then returned back to its original position for the duration of flexion. Similarly, such a configuration also ensures that the cam follower 170 is briefly urged from an original, or neutral, position toward the pivot portion 132 of the cam plate 130 during the final stage of extension of a patient's knee and then returned back to its original position once fully extended.

Each segment 26A, 26B of the elongate element is securely coupled to a respective hinge assembly by a connector 186 at the first end 182 of the piston 180. The connector 186 may include apertures for tying the elongate element thereto. The initial tension in each segment 26A, 26B of the elongate element is set by the adjustment mechanism 18. As the cam follower 170 is pulled toward the pivot portion 132 of the cam plate 130, the elongate element is likewise pulled taut increasing the tension in the elongate element. This increase in tension correspondingly causes the tibial shell 32 to exert additional posteriorly directed force against the anterior tibia to urge the tibia posteriorly.

The aforementioned known hinge structures may be in combination with the cam assembly whereby the cam plate is secured to a hinge component or the upper frame or strut and the cam follower secures to the lower frame or strut. Regardless on the type of hinge structure employed, the cam assembly tracks the articulation of the upper strut relative to the lower strut and enables selective and dynamic control of the elongate element and the tibial shell.

Figure 10:
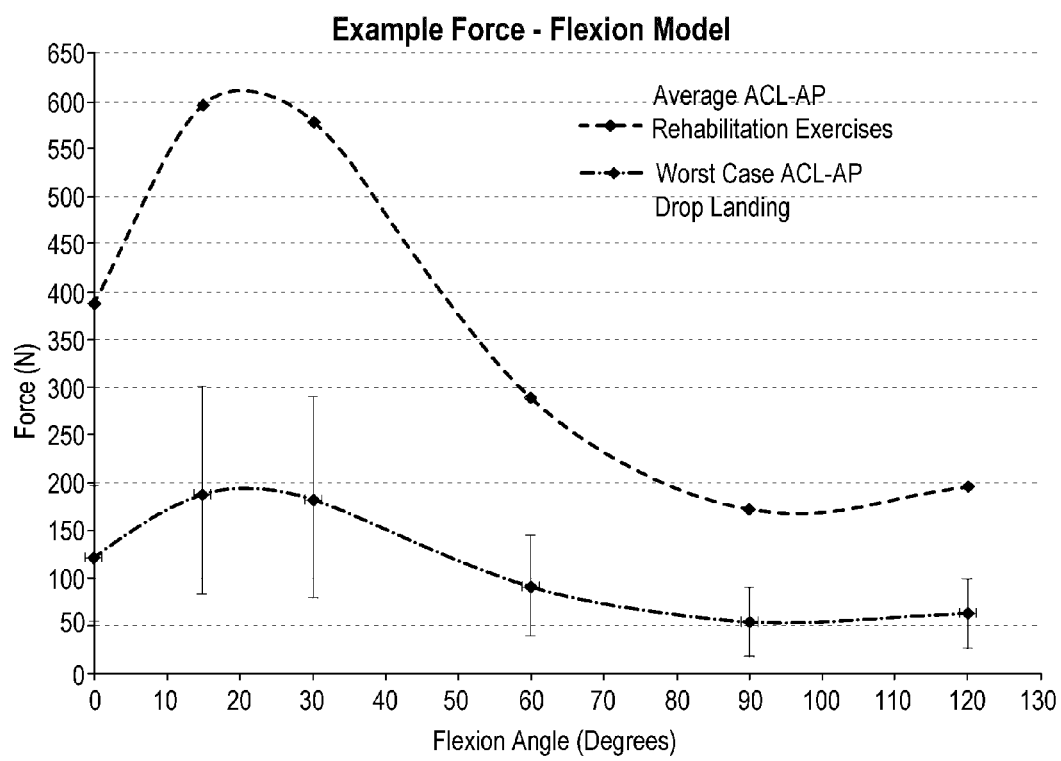
FIG. 10 is a graph depicting the force applied to an ACL versus its flexion angle as a knee is flexed in an exemplary "ACL tension curve."

In referring to ACL tension curve FIG. 10, a graph shows the loading on a patient's injured ACL and its corresponding angle of flexion. The top curve denotes the force on an average ACL during rehabilitation exercises, and the bottom curve denotes the force on a worst case ACL drop landing. The loading is plotted against the angle of flexion of a patient's knee. From these curves, peak loading occurs in both situations during the initial stage of flexion, making it the most dangerous.

Extension generally occurs at 0 degrees with the leg and orthopedic device in a fully or substantially upright formation. As the hinge assembly articulates, the orthopedic device undergoes flexion over a plurality of angles. Maximum flexion is referred to herein at about 135 degrees, however, flexion may still continue to occur past 135 degrees in FIG. 10, and may vary from individual to individual. The force required may gradually increase past 90 degrees after having diminished approaching 90 degrees as the maximum flexion serves in part as an inflection point on the curve in FIG. 10.

The eccentric shape of the guide slot 134 of the cam plate 130 preferably provides up to twenty degrees of additional tensioning in the elongate element 26 during the most dangerous stage of flexion and extension of a patient's knee. The eccentric shape of the guide slot 134 ensures that the additional posteriorly directed force is applied by the tibial shell only during the initial stage of flexion and the final stage of extension of a patient's knee. This posteriorly directed force exerted by the tibial shell would advantageously neutralize the ACL force in the anterior direction by resisting movement of the tibia toward the anterior direction relative to the femur at its most vulnerable angles.

Figure 6:
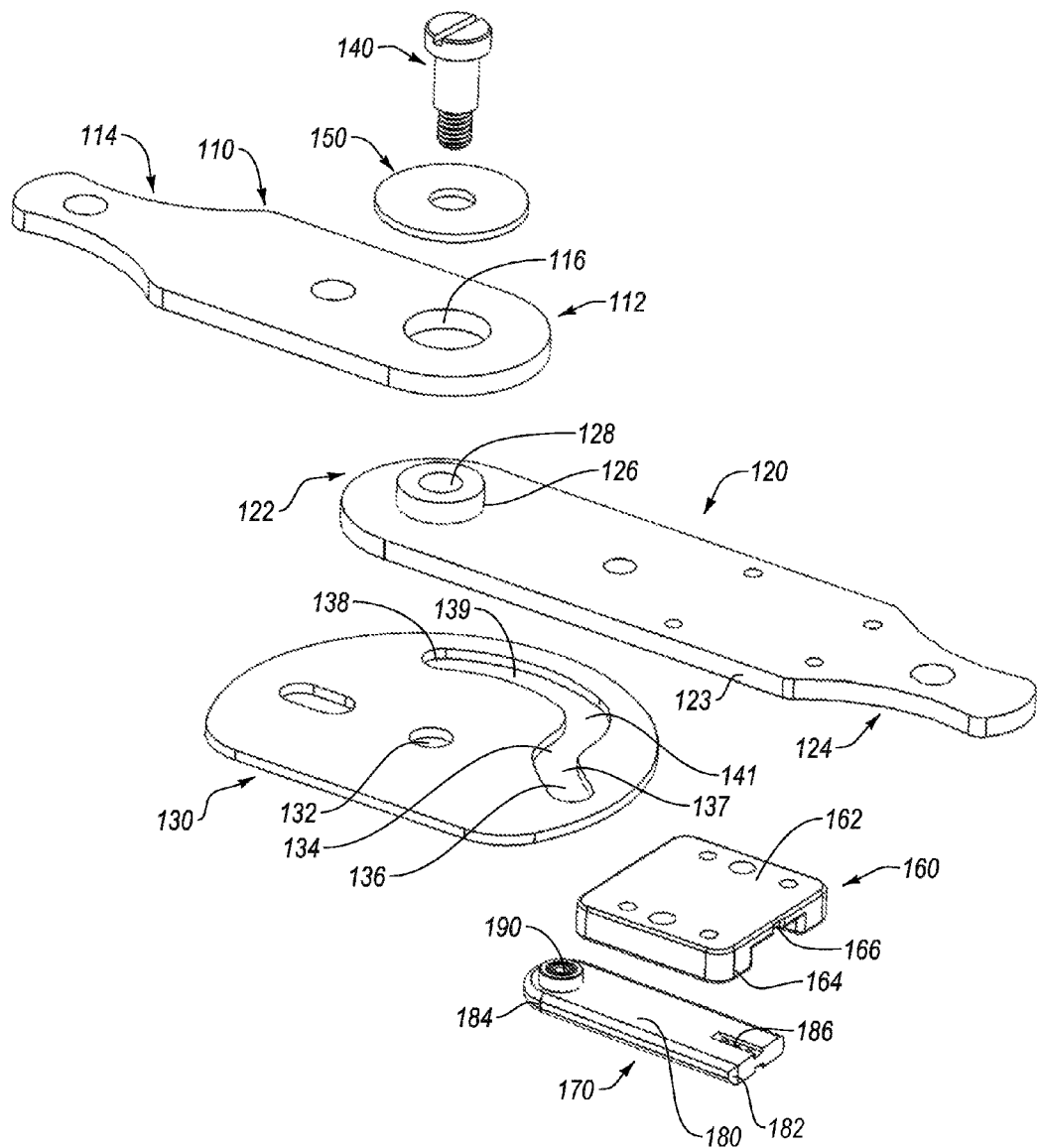
FIG. 6 is an exploded view of the hinge assembly of FIG. 5
Figure 9:
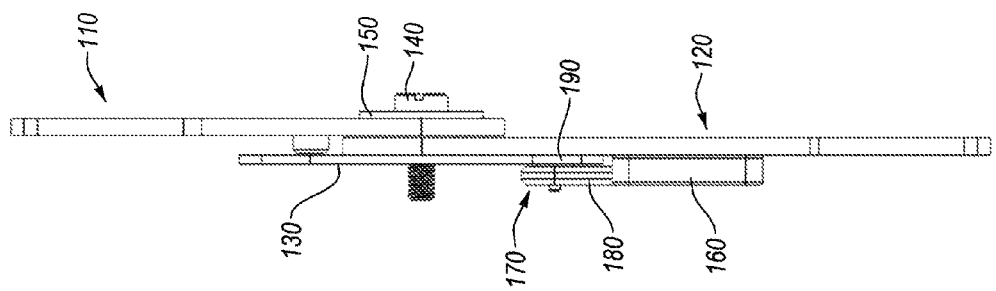
FIG. 9 is a side elevational view of the hinge assembly of FIG. 5.
Figure 8:
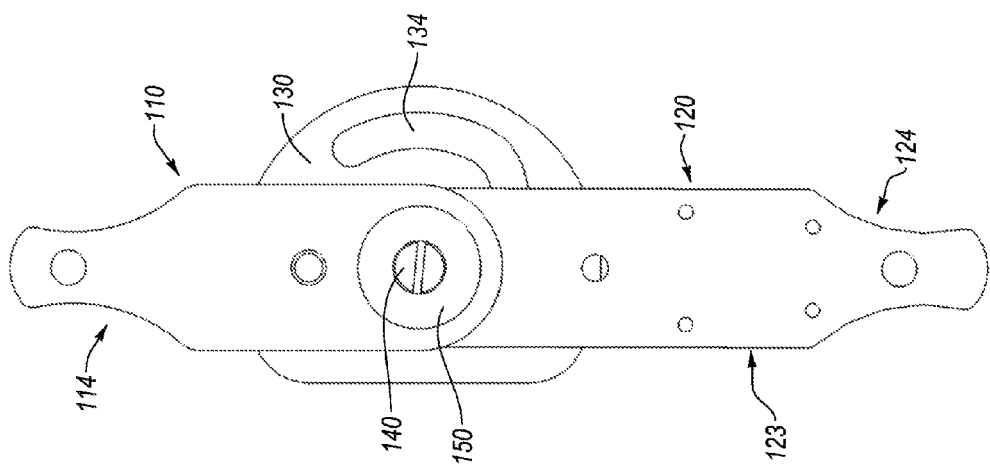
FIG. 8 is a rear elevational view of the hinge assembly of FIG. 5.
Figure 7:
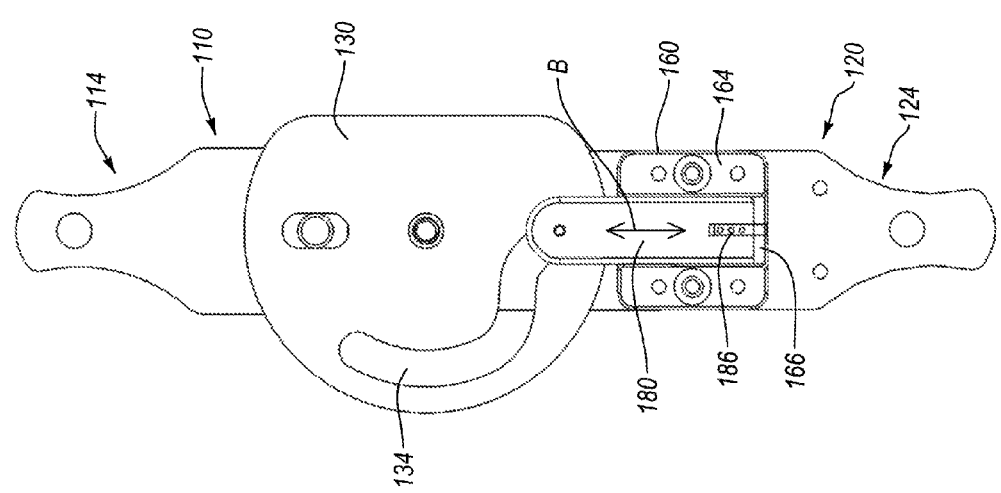
FIG. 7 is a front elevational view of the hinge assembly of FIG. 5.

In referring to the shape of FIG. 6, the shape of the guide slot 134 involves a first segment 137 encompassing the first end 136. The first segment 137 extends upwardly or toward the upper strut 110 at an oblique angle generally extending toward the posterior side P of the hinge assembly relative to an axis A-A representing extension of the hinge assembly. The first segment 137 is arranged to generally correspond to approximately 0 to 15 degrees of flexion, as corresponding to the slope in the ACL tension curve of FIG. 10 to generate force. The first segment 137 may extend generally linearly from the first end 136 to a transition segment 141 of the guide slot.

The transition segment 141 generally corresponds from 10 to 40 degrees of flexion so as to create an increase in force and then taper in force as the hinge assembly goes into greater flexion. The guide slot 134 includes a second segment 139 encompassing the second end 138 and representing a diminution in force generated as the knee goes into greater flexion as the cam follower travels to the second end 138. The second segment 139 generally extends arcuately from the transition segment 141, which is arranged to smooth the transition between the paths of the first and second segments 137, 139.

Figure 11:
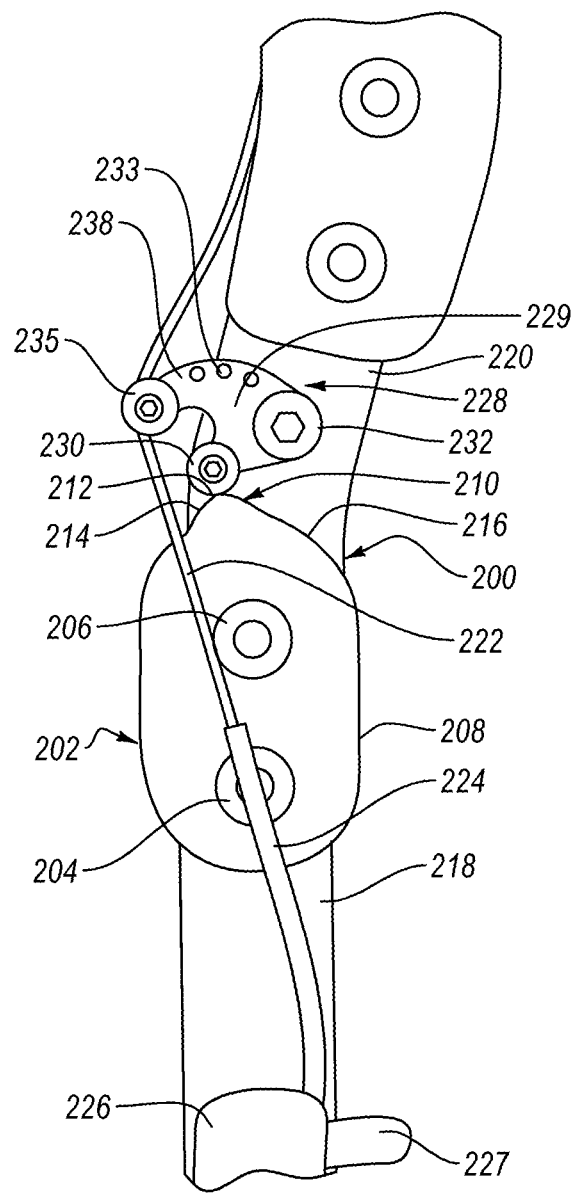
FIG. 11 is a sectional view showing another hinge assembly embodiment.

Another hinge assembly or adjustment device embodiment 200 is depicted in FIG. 11. This hinge assembly relies on using "follower" tracks with a cam assembly and a follower defined along the periphery of a hinge element, such as a plate. The cam assembly mimics the load curve as generally referred in the ACL tension curve of FIG. 10 to increase and decrease a load in combination with a cable and a dynamic shell depending on flexion. The dynamic loading component can load the tibia or the femur depending on the orientation of the cam assembly and the cam follower.

The hinge assembly 200 includes a polycentric hinge 202 having first and second pivot points 204, 206, and a hinge element 208, preferably defined as a hinge plate. The hinge element 208 defines a cam surface 210 arranged to mimic the load curve defined in the ACL tension curve of FIG. 10. A peak 212 defined by the cam surface 210 represents the maximum load exerted by the dynamic loading component 227, whereas the sloping segments 214, 216 represent gradually changing loads extending from the peak load 212.

The hinge assembly includes first and second struts 218, 220 connecting to the hinge 202. The first and second struts 218, 220 may be formed from an orthopedic device frame, or the first and second struts 218, 220 may secure to upper and lower frames, such as those in FIG. 1.

A cable 222 connects at one end to the dynamic loading component 227, extends and is routed through a cable guide 224 to a cable anchor 235 carried by the cam assembly 228. In this embodiment, the cable 222 extends over the hinge 202 and moves relative thereto according to the angle of flexion the hinge undergoes. The cam assembly 228 includes a cam follower 230 arranged to move and engage the cam surface 210. The cam assembly 228 is pivotally mounted on the upper strut 220 by a pivot element 232 to accommodate movement of the hinge 202 and the cam follower 230 relative to the cam surface 210.

The cam assembly 228 includes a plate 229 carrying the cam follower 230, the pivot element 232 and the cable anchor 235. The plate 229 defines an arm 238 extending from the pivot element 232 and defining a plurality of openings 233 for variable placement of the cable anchor 235 for different predetermined tension settings of the cable 222.

Figure 12:
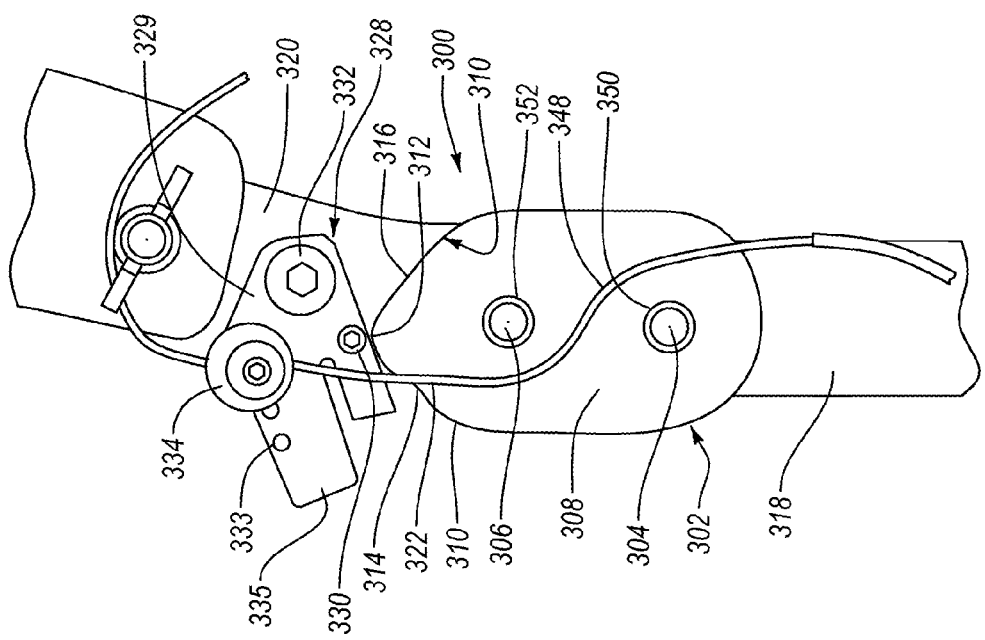
FIG. 12 is a sectional view showing another hinge assembly embodiment.

FIG. 12 represents an adjustment device or hinge assembly embodiment 300 that is a variation of the hinge assembly 200 of FIG. 11. The hinge assembly 300 includes a polycentric hinge 302 and first and second pivot points 304, 306. The hinge 302 includes a hinge element 308, preferably defined as a hinge plate. The hinge element 308 defines a cam surface 310 arranged to mimic the load curve defined in FIG. 10. A peak 312 defined by the cam surface 310 represents the maximum load exerted by the dynamic loading component (not shown), whereas the sloping segments 314, 316 represent gradually changing loads extending from the peak load 312.

The hinge assembly 300 includes first and second struts 318, 320 connecting to the hinge 302. The first and second struts 318, 320 may be formed from an orthopedic device frame, or the first and second struts 318, 320 may secure to upper and lower frames, such as those in FIG. 1.

A cable 322 connects at one end to the dynamic loading component (not shown, but using the guide of FIG. 11 as an example), extends and is routed through a cable guide (not shown, but using the guide of FIG. 11 as an example) to a cable anchor 334 carried by a cam assembly 328. In this embodiment, the cable 322 extends over the hinge 302 and moves relative thereto according to the angle of flexion the hinge undergoes. The cam assembly 328 includes a cam follower 330 arranged to move along and engage the cam surface 310. The cam assembly 328 is pivotally mounted on the upper strut 320 by a pivot element 332 to accommodate movement of the hinge 302 and the cam follower 330 relative to the cam surface 310.

The cam assembly 328 includes a plate 329 carrying the follower 330, the pivot element 332 and the cable anchor 334. The plate 329 defines an arm 335 extending from the pivot element 332 and defining a plurality of openings 333 for variable placement of the cable anchor 334 for different predetermined tension settings of the cable 322.

The hinge assembly 300 includes first and second routing parts 350, 352 extending from the hinge element 308. In a preferred embodiment, the routing parts 350, 352 include a washer and fastener, as depicted in FIG. 12, although other types of routing parts are envisioned and capable of routing the cable over the hinge element. The cable 322 extends about the routing parts 350, 352 and forms an "S" shaped cable path, although other shaped paths are envisioned.

The cable path about the routing parts forms a "zero-slack" path allowing the cable to be tensioned and remain in tension during flexion to extension. This arrangement permits achieving the desirable limit or threshold loading at extension. The cam assembly and hinge element profile allow for tension in the cable to ramp up to a maximum load at a predetermined flexion angle and then reduce in load after the peak is achieved.

Figure 13:
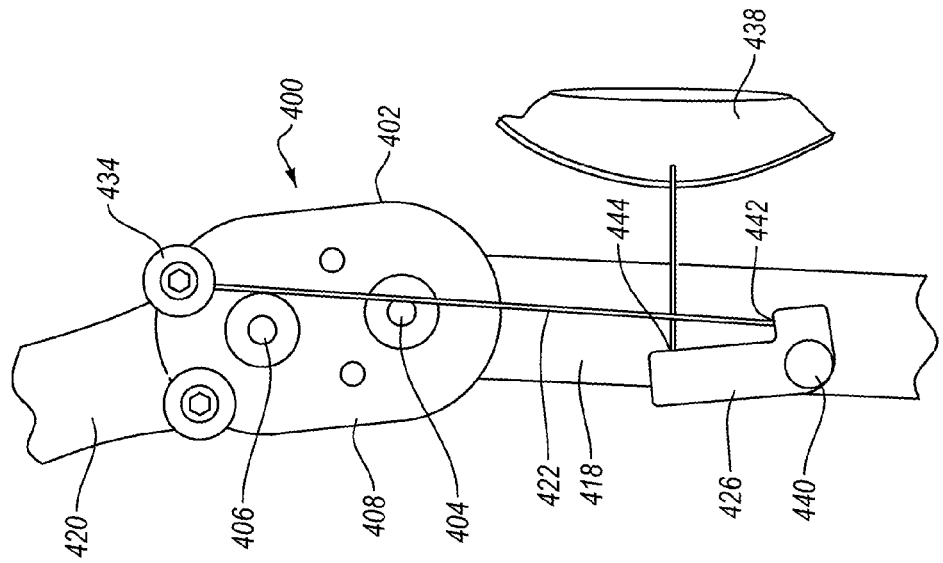
FIG. 13 is a sectional view showing another hinge assembly embodiment.

FIG. 13 shows another hinge assembly or adjustment device embodiment 400. The hinge assembly 400 includes a polycentric hinge 402 and first and second pivot points 404, 406. The hinge 402 includes a hinge element 408 upon which the first and second pivot points 404, 406 are located.

As with other hinge assembly embodiments, the hinge assembly 400 includes first and second struts 418, 420 connecting to the hinge 402. The first and second struts 418, 420 may be formed from an orthopedic device frame, or the first and second struts 418, 420 may secure to upper and lower frames, such as those in FIG. 1.

A link 422 connects at one end to a cable anchor 434 and extends to a multiplier element 426. The multiplier element 426 is arranged to increase the tension in a cable extending to the dynamic loading component 438. The link 422 may be a cable, strut, or other device connecting to the multiplier element 426. The multiplier element 426 is preferably pivotably mounted on the first strut 418 and is pivotable relative to the hinge 402.

In a variation, the multiplier element may be arranged to yield under predetermined loads to prevent excessive loads exerted by the dynamic loading component. It may be constructed from a plastic that will bend or yield at a certain load to serve as a safeguard against overloading by the dynamic loading component.

The hinge element 408 and the upper strut 420 in a polycentric hinge move at different angular rates when compared to the lower strut 418. Because the hinge element 408 moves at half the angular distance as the upper lower strut for a 90 degree motion (sitting to standing), the L-shape of the multiplier element serves as a multiplier to increase the amount the cable 422 pulls. The peak cable tension may be achieved generally when the cable path passes over the lower pivot 404.

Figure 14:
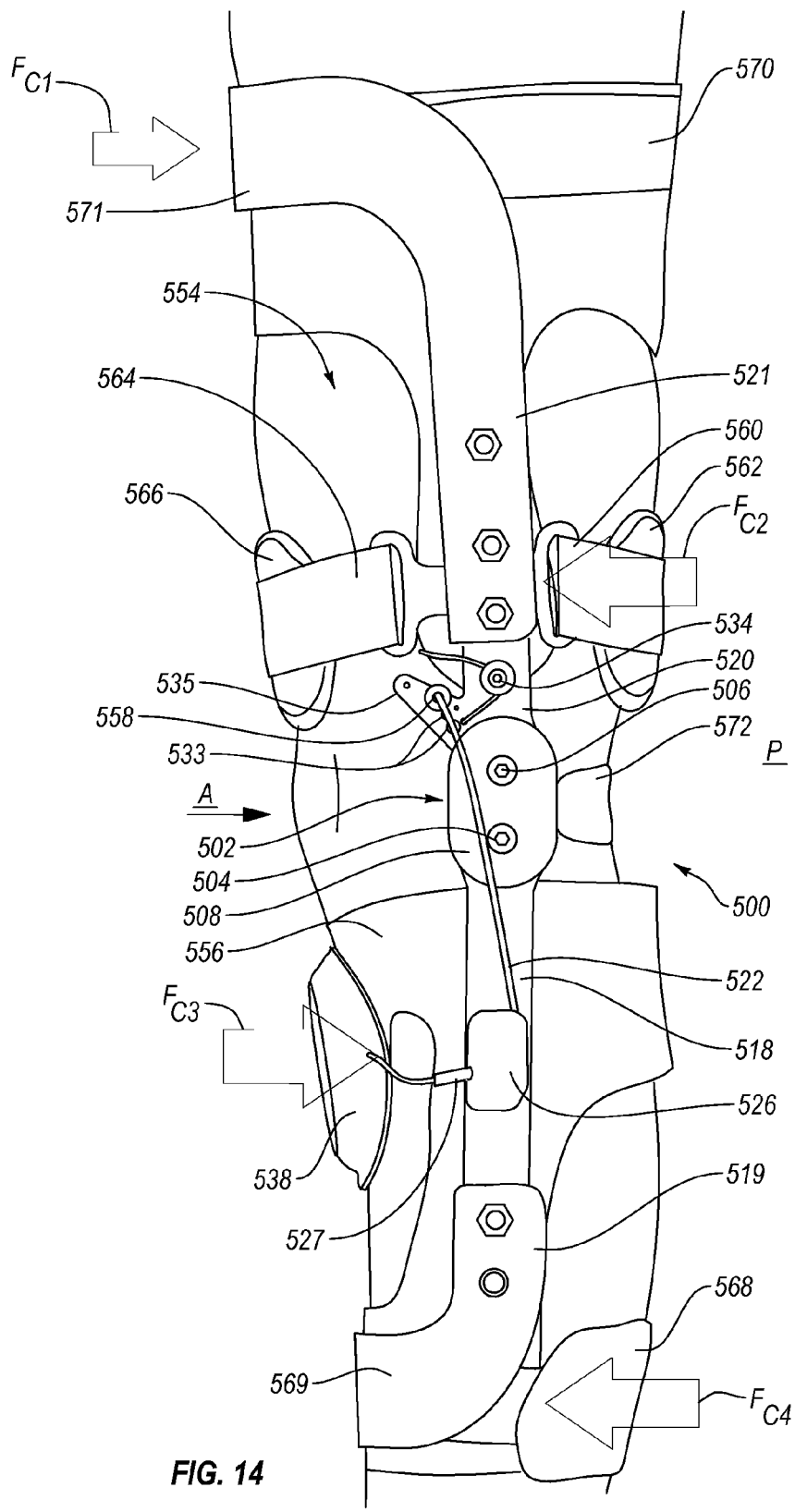
FIG. 14 is a side elevational view showing an orthopedic device having another hinge assembly embodiment.

FIG. 14 illustrates a hinge assembly or adjustment device 500 on an orthopedic device 554. Similar to other hinge assembly embodiments, the hinge assembly 500 includes a polycentric hinge 502 and first and second pivot points 504, 506. The hinge 502 includes a hinge element 508 upon which the first and second pivot points 504, 506 are located. The hinge assembly 500 includes first and second struts 518, 520 connecting to the hinge 502. The first and second struts 518, 520 may be formed from an orthopedic device frame, or the first and second struts 518, 520 may secure to upper and lower frames, such as those in FIG. 1.

A cable 522 connects at one end to the dynamic loading component 538, extends and is routed through an elongate portion 527 of a cable guide 526 to a cable anchor 534 carried by the second strut 520. The cable 522 is arranged to move and extend over the hinge element 508 at various flexion angles of the hinge 502. A cable plate 535 may be mounted on the second strut 520 and have an arm with adjustment holes 533. A route part 558 is mountable to one of the adjustment holes to allow for selective tensioning of the cable 522. The route part 558 diverts the cable over the cable plate 535, and the cable 522 extends to the anchor 534.

According to this hinge assembly, the cable crosses over the hinge, such that as the hinge passes through an instantaneous center of the hinge, the cable switches from loading to unloading (increasing to decreasing in length). From this arrangement, the load increases from 90 degrees flexion up to approximately 30 degrees flexion, and then decreases in load from approximately 30 to 0 degrees to full extension, mimicking the ACL tension curve of FIG. 10.

As shown in FIG. 14, the orthopedic device 554 includes lower and upper frames 519, 521, extending from the first and second struts 518, 520, respectively. While in this embodiment the lower frame 519 includes an anterior portion 569, and the upper frame 521 likewise includes an anterior portion 571, the lower and upper frames can be modified to extend over the posterior leg rather than the anterior leg, as depicted.

Various straps are provided to counteract the lower and upper frames, and the load exerted by the dynamic loading component. Front strap 564 having a pad 566, and rear strap 560 having a rear pad 562 are arranged on the upper frame 521. An upper wrap 570 extends opposite the upper frame 521, whereas a wrap 556 extends generally circumferentially about the lower leg from the dynamic loading component. A lower rear strap 568 extends generally opposite the lower frame 519.

The orthopedic device generally provides a dual 3-point system femoral support. Counter force Fc1 is provided at the anterior portion 571 of the upper frame 521, followed by a counter force Fc2 at the rear strap 560 with the front strap 564 resisting the rear strap 560. The lower strap 568 provides a counter force Fc4. The dynamical loading element 538 provides a load or force Fc3 resisted by the other counterforces, which urges the tibia in a rearward, posterior direction while being resisted by the aforementioned counterforces. The counter forces Fc1 and Fc3 resist Fc2, whereas the counter forces Fc2 and Fc4 resist the counter force Fc3 to provide the dual 3-point system. The forces work in tandem to apply approximate forces on the femur and tibia while maintaining the brace on the leg.

Figure 15:
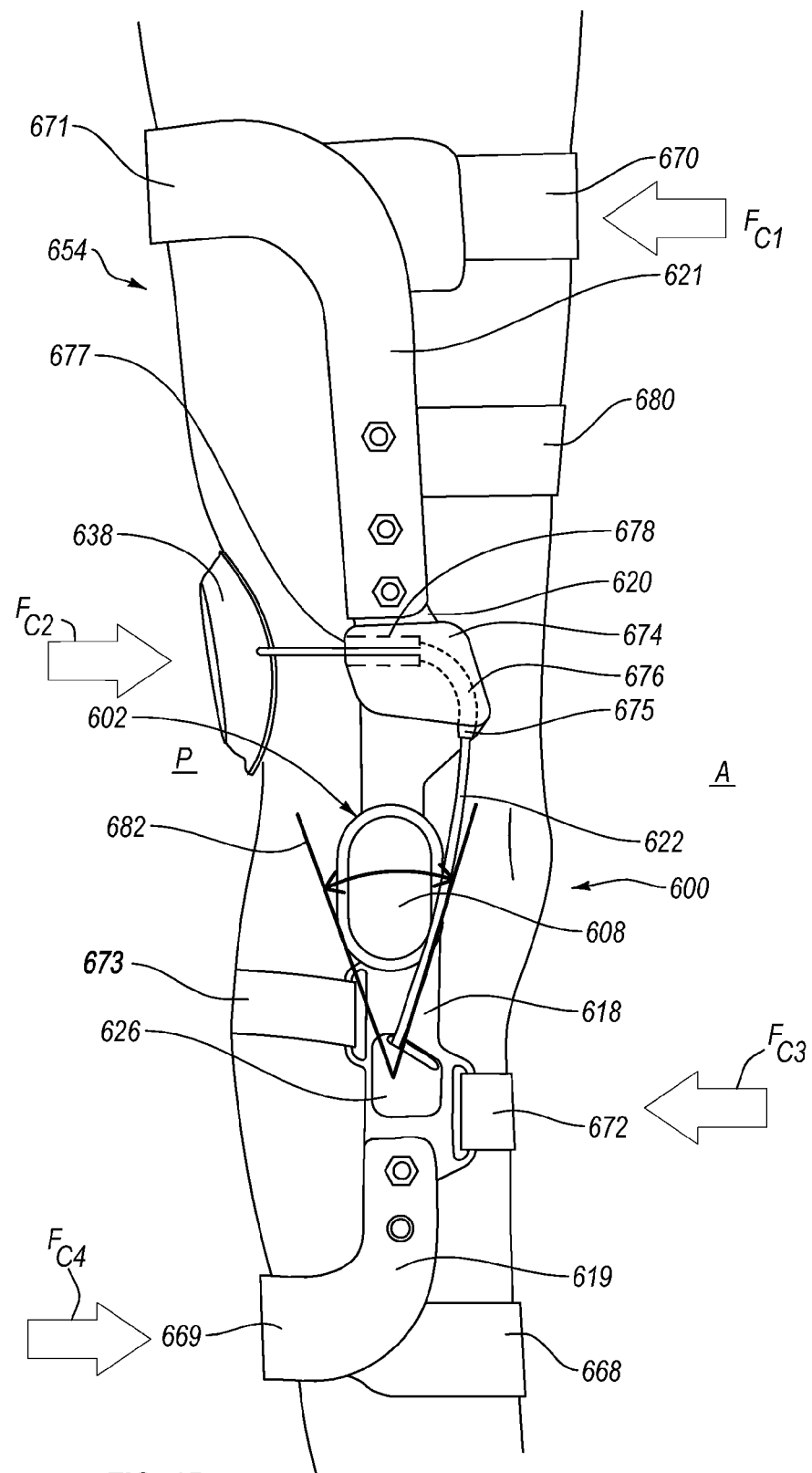
FIG. 15 is a side elevational view showing an orthopedic device having another hinge assembly embodiment.
Figures 16A, 16B:
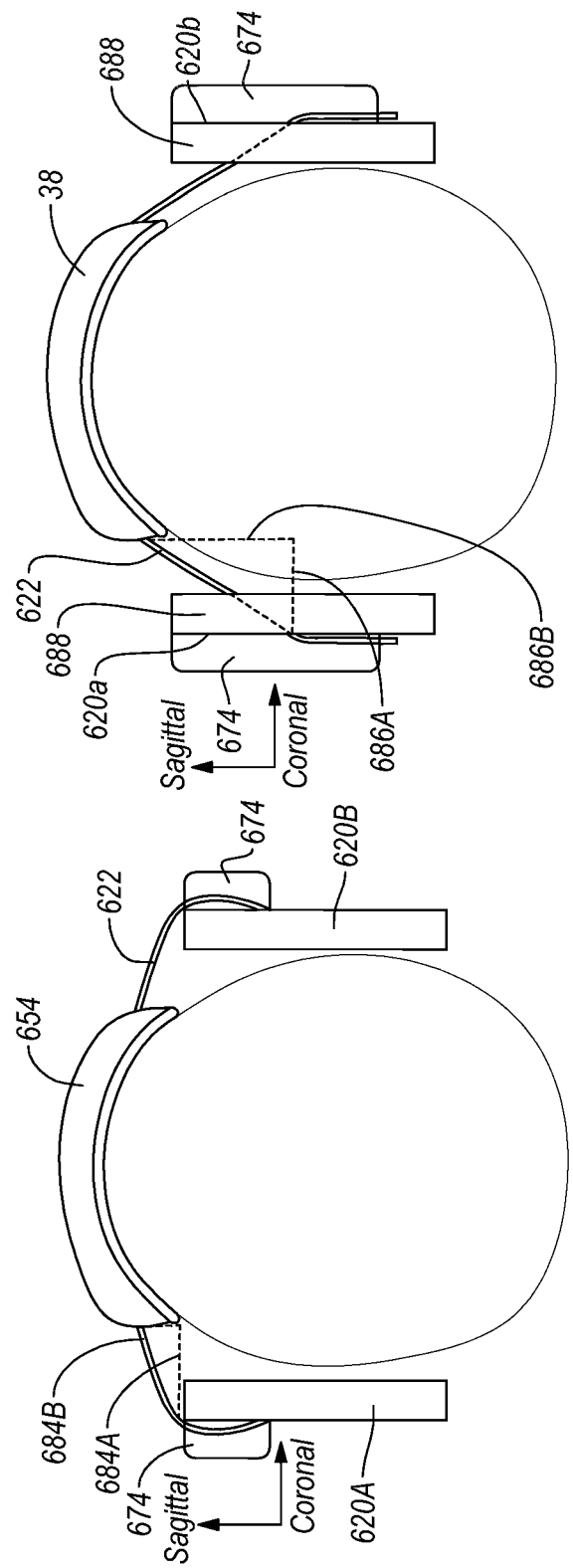
FIGS. 16A and 16B show views comparing different hinge assembly embodiments.

FIG. 15 illustrates another hinge assembly or adjustment device 600 on an orthopedic device 654 providing a dual 3-point system as in the embodiment of FIG. 14. Suitable straps 668, 670, 672, 680 are provided for securing the orthopedic device to the leg. In this embodiment, however, the lower and upper frames 619, 621 have posterior portions 669, 671, respectively, over the posterior side of the leg, and the dynamic loading component 638 is arranged to be located on the distal posterior thigh but is arranged not to impinge the popliteal of the user. FIGS. 16A and 16B depict the dynamic loading component 654 extending on the posterior side of a leg between the first and second upper struts 620A, 620B. As with the embodiment of FIG. 14, the counter forces Fc1 and Fc3 resist Fc2, whereas the counter forces Fc2 and Fc4 resist the counter force Fc3 to provide the dual 3-point system.

As in FIG. 15, the dynamic loading component 638 is connected to the upper frame 621 and located on an anterior or posterior side of the orthopedic device 654 between the upper frame 621 and the hinge element 608. A variable distance is defined between the dynamic loading component 638 and the upper frame 621 such that the dynamic loading component 638 is adapted to exert a first load in a sagittal plane relative to the coronal plane, as exemplified in FIGS. 16A and 16B.

The cable 622 is extended over the hinge element 608 and has a movement profile 682 permitting movement over flexion to extension and so forth. The movement profile generally forms a "V" shape and substantially extends from anterior and posterior peripheral sides of the hinge element 608 while the crest of the V-shape is anchored at the lower guide 626. The hinge element 608 preferably is a low profile to permit the cable 622 to sweep over the hinge element 608 during flexion with the lower cable guide serving as the pivot point.

The arrangement of the orthopedic device is such that the dynamic loading component loads proximally above the knee and has the advantage of preventing migration of the orthopedic device on the leg of the user. As the dynamic loading component urges a load above the knee at the femur, downward migration of the orthopedic device is minimized. The tendency of distal migration is reduced with a posteriorly positioned femoral load versus an anterior positioned tibia load while a user is seated generally at 90 degrees flexion. An anteriorly positioned tibia load will have the tendency to drive the orthopedic device downwardly and distally with respect to the leg. An anti-migration strap 673 may be used for the lower strut 618 to keep the orthopedic device from migration, and the strap 673 is arranged to rest along or above the belly of a user's calf to minimize sliding down the lower leg.

The hinge assembly 600 includes a hinge 602 that may be arranged in other embodiments described, and includes a hinge element 608 defined over the outer surface of the hinge 602. The cable 622 extends from the cable guide 626 on the first or lower strut 618 or lower frame 619. The cable 622 preferably extends to an upper cable guide 674 on the second or upper strut 620 or the upper frame 621 at inlet 675 generally located on the front or anterior side of the second strut 620. The cable 622 extends generally perpendicularly through a cable channel 676 defined by at least the upper cable guide 674 and exits the cable guide 674 at the posterior side of the upper cable guide 674 at outlet 677 to extend to the dynamic loading component 638.

As in FIG. 15, the upper cable guide 674 is connected to the upper frame 621. The inlet 675 is located on a first side of the upper cable guide 674 and extends beyond the first side of the coronal plane and the hinge element 608 along the sagittal plane, and the outlet 677 extends on the second side of the orthopedic device to direct the cable 622 along the sagittal plane toward the dynamic loading component 638. The cable extends generally perpendicularly from the inlet 675 to the outlet 677.

In any of the embodiments described herein, selective preset tensioning of the cable may be achieved at the dynamic loading element. As discussed more fully in U.S. provisional application No. 61/838,217, filed on Jun. 21, 2013, and incorporated herein by reference, the dynamic loading system may include a load-limiting clutch for tensioning the ends of the pair of cables (from both sides of the orthopedic device) extending into the dynamic loading element.

Figures 17A, 17B, 17C:
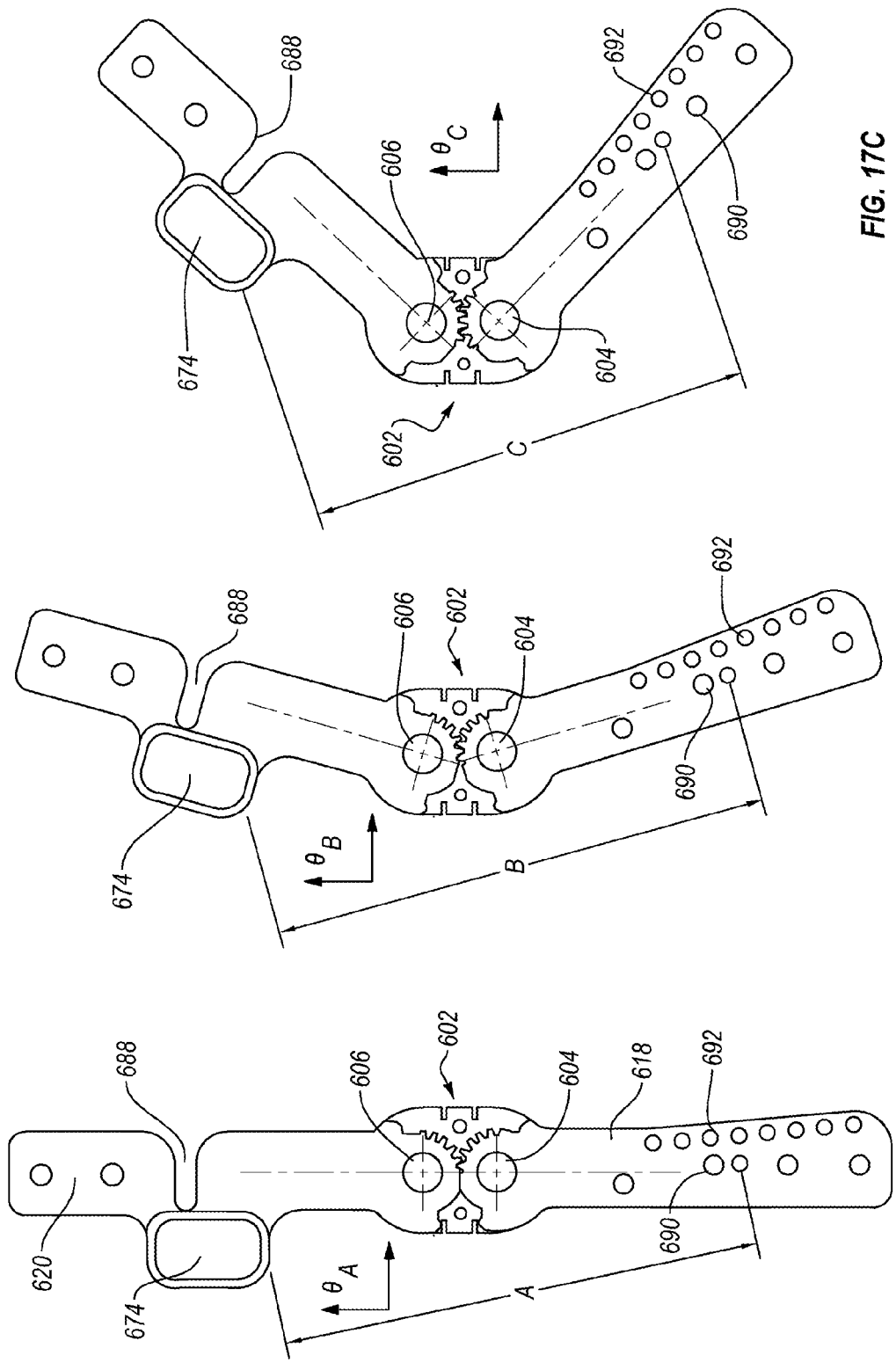
FIGS. 17A-17C show views comparing different angles of a hinge assembly embodiment.

As shown in FIGS. 17A-17C, the second strut or upright 620 to the orthopedic device includes a cutout 688 corresponding to the upper cable guide 674 and corresponding channel 678. The cutout 688 is generally arranged in the saggital plane and not the coronal plane. In an alternate embodiment, the cutout may be provided on the first strut or upright 618 when the dynamic loading component is urged against the tibia.

MCL injuries are often concurrent with ACL injury and therefore reduction of medial/lateral compression minimizes contact pressure on these injured regions. As shown in FIG. 16A, if the cutout is not present, the cable load is mainly in the coronal plane with the hinge assembly and orthopedic device loading in the coronal plane instead of loading the posterior femur in the saggital plane in FIG. 16B. FIG. 16A shows how the cable 622 must extend about the pair of second struts 620A, 620B and the majority of loading occurs in the coronal plane as depicted by the coronal force component 684A being greater than the saggital force component 684B. FIG. 16B shows how the cutout 688 allows for more loading in the saggital plane by the schematic 686. The saggital force component 686B is greater than the coronal force component 686A.

MCL injuries are often concurrent with ACL injury and therefore reduction of medial/lateral compression minimizes contact pressure on these injured regions. As shown in FIG. 16A, if the cutout is not present, the cable load is mainly in the coronal plane with the hinge assembly and orthopedic device loading in the coronal plane instead of loading the posterior femur in the saggital plane in FIG. 16B. FIG. 15 and FIG. 16A depict how the cable 622 must extend about the first and second upper struts 620A, 620B of the upper frame 621 on opposed sides of the orthopedic device generally along the coronal plane and supporting a posterior portion of the upper frame 621 adapted to secure about a posterior leg. The majority of loading occurs in the coronal plane as depicted by the coronal force component 684A being greater than the saggital force component 684B. FIG. 16B shows how the cutout 688 allows for more loading in the saggital plane by the schematic 686. The saggital force component 686B is greater than the coronal force component 686A.

FIGS. 17A-17C illustrate how peak cable tension occurs as the cable passes over the instantaneous center of the hinge 602 and relative to pivot points 604, 606. In this embodiment, the upper guide 674 is arranged forward of the cutout 688 to enhance movement of the cable along the saggital plane. Each of the first and second struts 618, 620 include a plurality of openings 690, 692 for mounting the cable, such as by the cable guide. At extension at $\theta_A$, the cable length A is less than the cable length B at flexion with the predetermined angle $\theta_B$, such as 30 degrees. After the predetermined angle $\theta_B$, subsequent increased flexion angles $\theta_C$ result in a shortening of the cable length C. As shown, the cable tension relaxes toward extension and towards flexion before and after reaching the predetermined angle $\theta_B$. The cable length generally has the relationship wherein cable length A<cable length B>cable length C.

D. Experimental Data

The embodiments of the disclosure are arranged to encourage healing of the ACL, enhance knee stability, and reduce elongation of ligament post ACL rupture reconstruction. The embodiments achieve these objectives by dynamically loading the ACL and maintaining an anatomically correct relationship of the femur and tibia through rehabilitation. The embodiments are arranged to approximate a dynamic load that is similar to the ACL tension curve depicted in FIG. 10.

Referring to the exemplary embodiment in FIG. 15, the orthopedic device for achieving the above objectives employs at least a three point loading scheme wherein a femoral counterforce Fc1 and a tibial counterforce Fc3 are counteracted by the dynamic tension force Fc2 to maintain an anatomically correct relationship of the femur and tibia.

Certain tests were conducted on human patients wearing an orthopedic device similar to the embodiment depicted in FIG. 15 by conducting ACL load mapping. Dynamic loads were measured from full extension to full flexion. For the tests, each patient was fitted with a custom brace and a load cell was applied to the dynamic loading component to ascertain the load for each patient during flexion of the knee.

Data was obtained for each patient as the patient underwent even paced eccentric squats. Each patient started in extension against a 0 degree extension stop in a polycentric hinge assembly of the orthopedic device, and lowered himself at an even rate until reaching a 90 degree flexion stop present in the hinge assembly.

Figure 18:
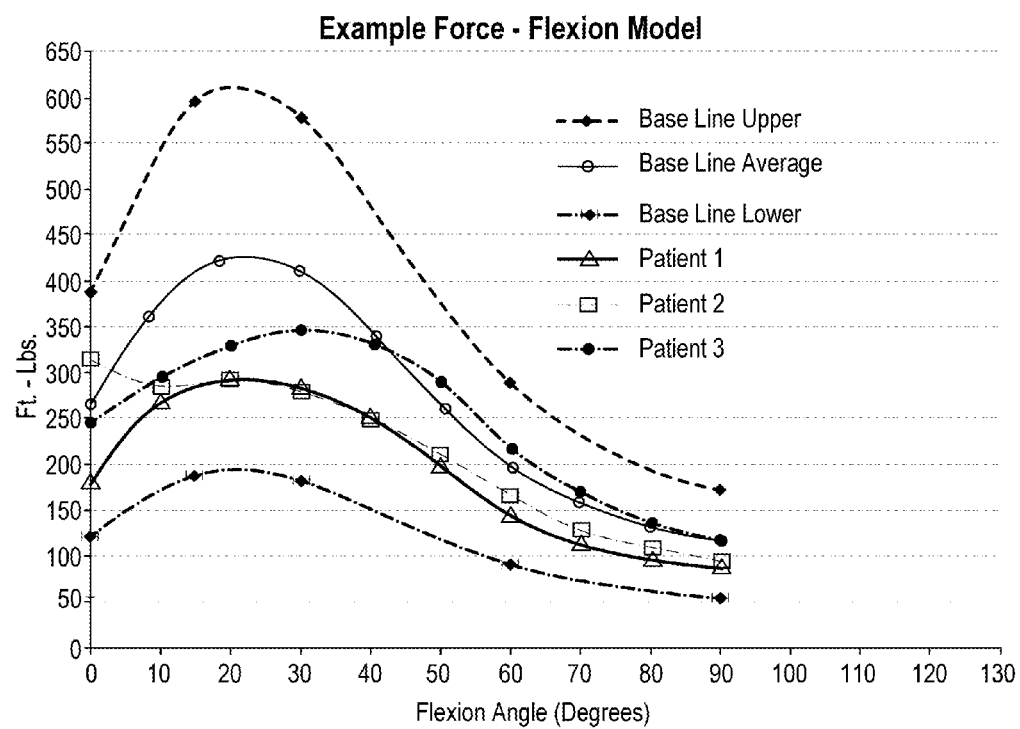
FIG. 18 is a version of the graph in the ACL tension curve of FIG. 10 including experimental data showing force versus flexion in embodiments of the disclosure.

FIG. 18 shows results from the tests and represents mean data. Each patient failed to reach a maximum or upper load, and rather each patient fell within the maximum and minimum ranges.

Patient 2 has a hyper-extended knee and this is the likely reason for the load curve between 0 degrees (maximum) to 10 degrees. The load curve may be normalized by placing a −10 degree extension stop rather than a 0 degree extension stop so at full extension the patient's leg is not resisting the brace frame in the manner represented by the data.

The results show that the orthopedic device imparts a dynamic load similar to the ACL tension curve of FIG. 10. Each patient (negating for the aberration with Patient 2) exhibits a maximum peak in the ACL tension curve at approximately the same flexion, with both a similar rise leading to the peak and a similar decline after the peak as the knee continues in flexion.

In each instance, the patient exhibited a lower load at full flexion (e.g., 90 degree flexion) than at full extension (0 degree flexion), with the load undergoing a drop-off from the peak. In each patient, the rise to the peak (generally 0 to 30 degrees) gradually inclines and tapers near or at the peak to generate the highest load, at the most important flexion angle. As the need for the load diminishes from the peak, the data shows that the load slowly declines in magnitude to full flexion (generally 30 to 90 degrees).

As shown in FIG. 18, the ACL tension curve for each patient is generally concave at initial loading but exhibits slight or gradual convex trends to full flexion from a particular inflection angle, varying by patient, forming an actual compound ACL tension curve. The convex nature is likely due to laxity of the soft muscle tissue about the knee and leg as the user surpasses the need for the peak load. The ACL tension curve trails off which allows for greater comfort and ease of musculature, ligaments, and cartilage to mitigate any damage to a rehabilitating knee while maintaining stability of the knee as the PCL is stretched, and other ligaments, as the ACL is unloaded.

Figure 19:
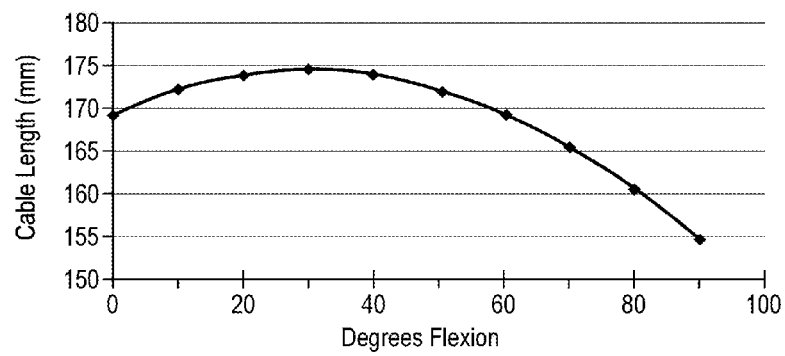
FIG. 19 is a graph showing cable length versus flexion in the embodiment of FIGS. 17A-17C.
Figure 20:
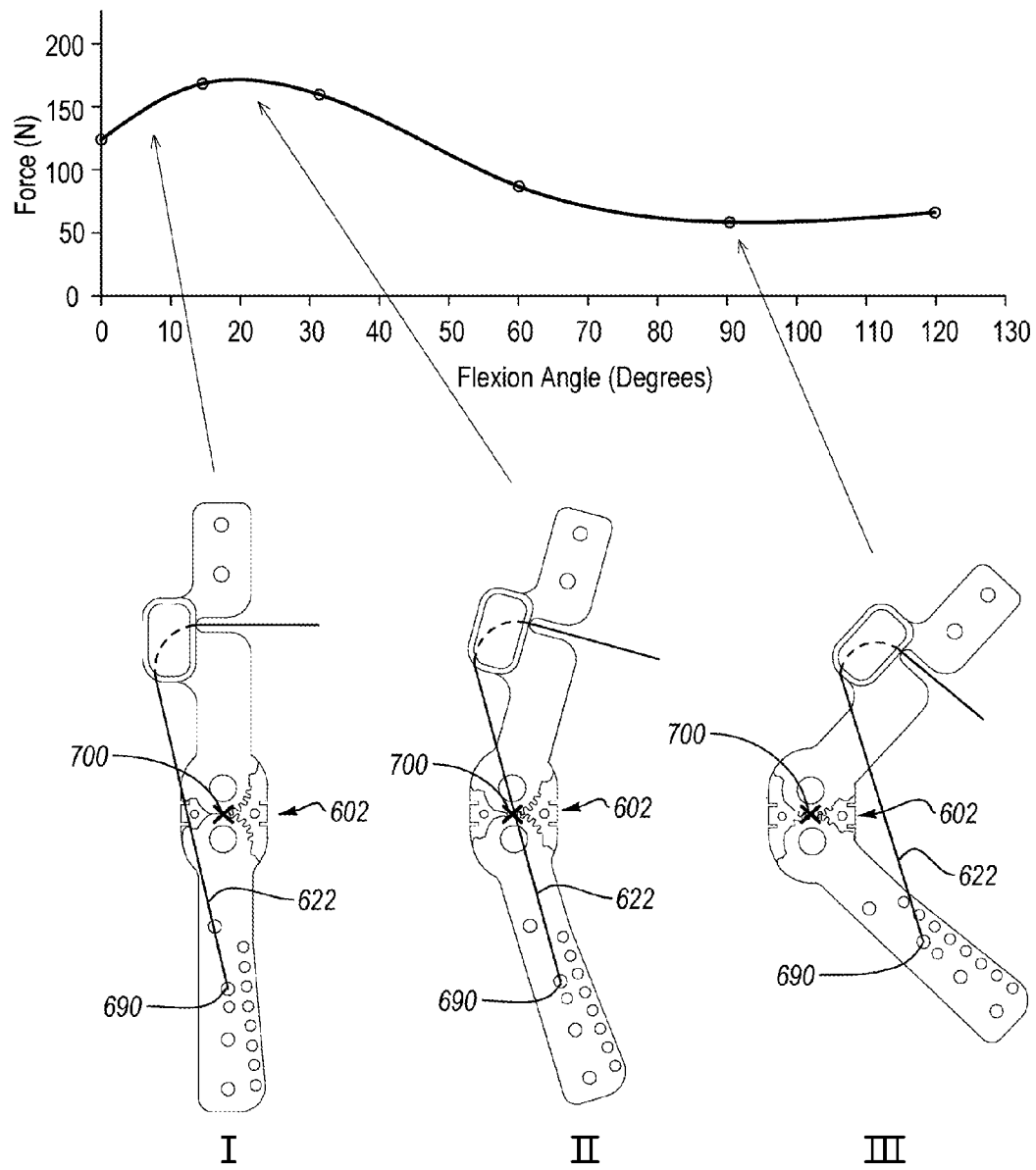
FIG. 20 is a schematic view showing the hinge assembly of FIGS. 17A-17C compared to the ACL tension curve of FIG. 10.

FIG. 19 shows the cable length as the knee flexes and is depicted without being placed on a patient. FIG. 20 exemplifies the cable in the hinge assembly of FIGS. 17A-17C compared to the ACL tension curve. The cable tension correlates to the peak load of the ACL tension curve because the maximum cable length occurs at the peak load, whereas the cable length at 0 degrees flexion is less than the peak load, but sharply more than the cable length at 90 degrees flexion. As with the ACL tension curve, the cable length gradually decreases in length after the peak load and toward full flexion as opposed to the cable length between full extension (0 degrees flexion) to the peak load.

Unlike in the patient data of FIG. 18, the cable length curve in FIG. 19 does not exhibit the same laxity in forming a slightly convex curve. Desirably, the drop off in the ACL tension curve on actual patients is more gradual than the cable length curve from the peak load to full flexion, although the cable length curve does not exhibit convex nature as the cable length reaches a minimum length. Again, the soft-tissue interaction with the orthopedic device as the cable length and load decrease desirably enables a smooth and gradual transition from the peak load and facilitates healing and mitigates damage to the knee.

FIG. 20 shows the cable 622 at a maximum length in Movement II and passing through the instantaneous center of rotation 700 of the polycentric hinge 602. In Movement I, the cable 622 is outside the hinge and instantaneous center of rotation, and is anteriorly located relative to the hinge 602 (referring to the embodiment of FIG. 15, orientation is reversed). In Movement III, whereat the cable 622 is at its shortest length, the cable 622 has swept from full extension to full flexion across the hinge 602 during hinge articulation. The movement of the hinge 602 and the lengthening and shortening of the cable 622, and regulation of initial tension in the cable by the dynamic loading component enable the dynamic nature of the peak load and the ACL tension curve.

It will be understood, the cable may be mounted at different locations along the hinge assembly to generate a peak load at different flexion angles and the methods and embodiments described are not limited to the specific loads and angles referred to above. Adjustments may be made to the cable mounting, hinge assembly and other components to accommodate movement and indications of an individual patient. Patient 2 in the study discussed above exhibits hyper-extension and adjustments may be made to the orthopedic device including the hinge assembly, as discussed, to more closely track the ACL tension curve.

Adjustments may be made on other components of the orthopedic device. The distance between a tibia shell and distal frame may be adjusted to prevent migration of the orthopedic device. Adjustment in location of the dynamic loading component for an individual may be made to adjust cable length or prevent migration of the orthopedic device on the wearer's leg, particularly on the posterior thigh which has an anatomical shape that traps or limits the brace from slipping due to the location of the knee.

The orthopedic device and methods are not limited to the ACL tension curve of FIG. 10. Methods may include maintaining a peak load to a point in flexion from full flexion to a specified flexion angle, and then enable linear dropping of the load after the peak load is achieved and the knee goes into further flexion.

E. Alternative Embodiments and Components

Figure 21:
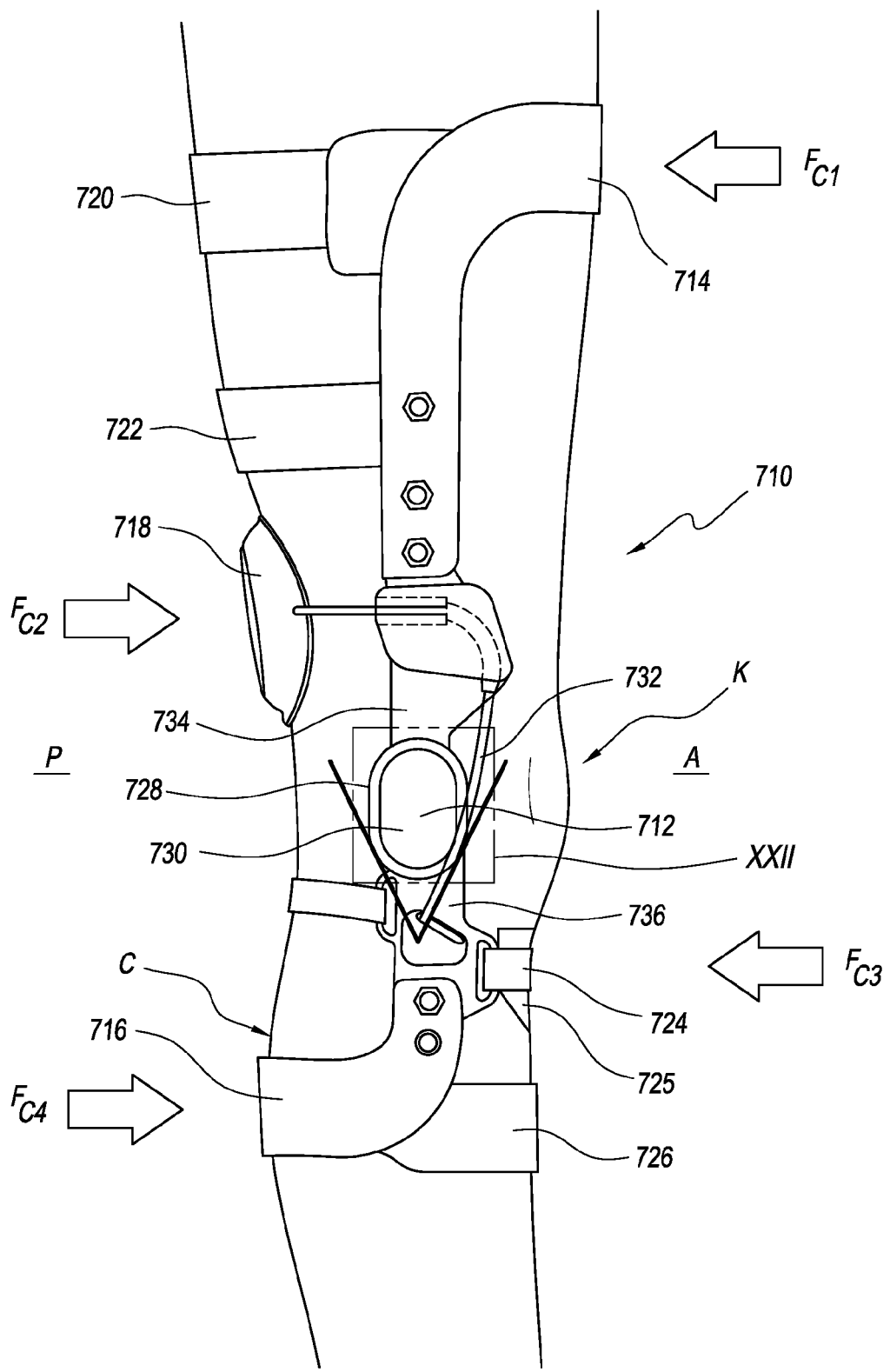
FIG. 21 is a side elevational view showing another embodiment of an orthopedic device having the hinge assembly of FIG. 15.

FIG. 21 shows an alternative embodiment of the orthopedic device, wherein the orthopedic device 710 includes an upper frame 714 arranged for extending about the anterior aspect A of the upper leg, a lower frame 716 arranged for extending about the posterior aspect P of the lower leg, and at least one hinge 712 connecting the upper and lower frames 714, 716. The upper frame 714 preferably extends about the anterior thigh of the user, whereas the lower frame 716 preferably extends about the posterior calf of the user, but is desirably raised to be close to the hinge axis than in other disclosed embodiments such as in the embodiment of FIG. 15.

The overall extension of the lower frame 716 is preferably shortened by either shortening the length of the lower strut 736 or the lower frame itself, and the upper frame 714 may likewise be shortened in length either itself or by shortening the upper strut 736. As shown, the dynamic loading component 718 is preferably located just above the posterior knee, and therefore enables overall shortening of the upper and lower frames 714, 716 relative to the knee K and the hinge 712. By placing the upper frame on the anterior side of the leg, there is better comfort to the user by taking advantage of more fleshy mass of the thigh on the anterior aspect. Likewise, by shortening the lower frame, the lower frame can extend about the fleshy mass of the calf C on the posterior aspect of the leg.

Suitable straps 720, 722, 726 are provided for securing the orthopedic device to the leg and a strap 724 is provided for counteracting forces applied according to the dynamic loading component 718 and articulation of the hinge 712. For example, the anterior strap 724 carries a tibial cuff 725 which combines with the anterior strap 724 to provide a tibial counterforce Fc3 with a femoral counterforce Fc1 for counteracting the dynamic force Fc2 urged by the dynamic loading component 718. The lower frame 716 over the calf offers a counterforce Fc4. As with the embodiment of FIG. 15, the counter forces Fc1 and Fc3 resist Fc2, whereas the counter forces Fc2 and Fc4 resist the counter force Fc3 to provide the dual 3-point system.

Figure 22:
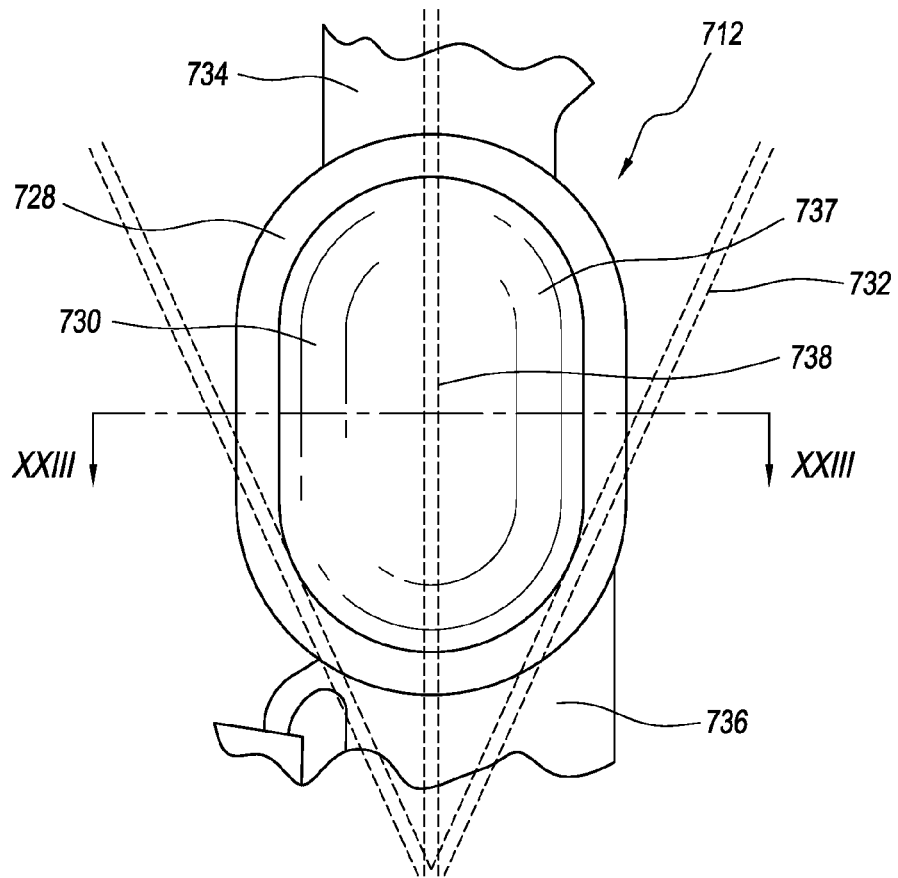
FIG. 22 is a detail view from FIG. 21 showing a hinge cover having a load adjuster.

Referring to the hinge 712, FIGS. 21-24 exemplify the concept of providing a load adjuster 730 to a hinge cover 728 of the hinge 712. The concept of the load adjuster 730 resides in increasing peak loading without adjusting the dynamic loading component by selectively creating a thicker hinge cover. As shown in FIG. 22, the cable 732 sweeps over an apex 738 of the load adjuster 730 over the hinge cover 728, with the hinge cover 728 and the load adjuster 730 forming a thickened region along the coronal plane.

Figure 23:
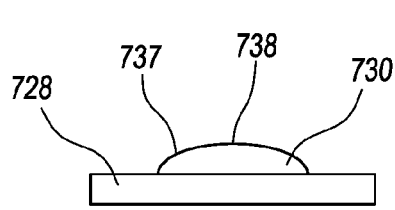
FIG. 23 is a cross-sectional view from FIG. 22 showing the load adjuster on a hinge cover.

As exemplified in FIG. 23, the load adjuster 730 may have rounded edges 737 leading to the apex 738 wherein the cable may roll over the load adjuster as if it is a speed bump, thereby creating cable excursion resulting in desired loads across the calf controlled by the slope together with pre and post apical forces. Alternatively, other shapes and configurations may be arranged for the load adjuster to achieve its desired purpose, and are not limited by the exemplary embodiments provided herein.

Figure 24:
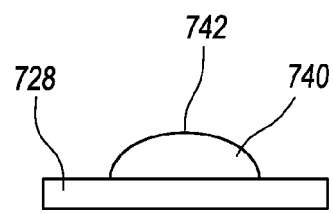
FIG. 24 is a cross-sectional view showing a variation of the load adjuster of FIG. 22.

While loading anteriorly, different shaped load adjusters may be provided to regulate medial or lateral cable sweep or medial/lateral cover speed bump thickness, as seen by the contrasting shapes between the load adjuster 730 in FIG. 23 and the load adjuster 740 in FIG. 24 with a higher apex 742 relative to the apex 738 in FIG. 23. According to the different shapes of load adjusters, differential sweeps or ultimate cable excursions may result in medially directed or laterally directed circumferential shear imparted by dynamic loading component to create tibial rotational control for the tibio/femoral relationship of the knee. Alternatively, the orthopedic device may be provided without the dynamic loading component, or at least one without a tensioning mechanism, which relies on different load adjuster shapes for creating the different cable sweeps.

While the foregoing embodiments have been described and shown, alternatives and modifications of these embodiments, such as those suggested by others, may be made to fall within the scope of the invention. While the orthopedic device has been described in a knee brace, it will be understood that the principles described may be extended to other types of orthopedic devices.

The invention claimed is:

1. An orthopedic device arranged to articulate from extension to flexion over a plurality of angles, the orthopedic device being divided into first and second sides by a coronal plane, the orthopedic device comprising:
   an upper frame;
   a lower frame;
   a hinge connecting the upper and lower frames to one another, the hinge defining an outer surface having first and second sides divided by the coronal plane intersecting with an instantaneous center of rotation;
   a dynamic loading component connected to the upper frame and located on an anterior or posterior side of the orthopedic device between the upper frame and the hinge, a variable distance being defined between the dynamic loading component and the upper frame such that the dynamic loading component is adapted to exert a first load in a sagittal plane relative to the coronal plane;
   at least one elongate element having a first end connected to the dynamic loading component and a second end secured to the lower frame, the at least one elongate element arranged to extend over the outer surface of the hinge as the orthopedic device articulates;
   an upper cable guide connected to the upper frame, the upper cable guide having an inlet located on a first side of the upper cable guide and extending beyond the first side of the coronal plane and the hinge along the sagittal plane, and an outlet extending on the second side of the orthopedic device and directing the at least one elongate element along the sagittal plane toward the dynamic loading component, the at least one elongate element extending generally perpendicularly from the inlet to the outlet
   wherein when the orthopedic device is in extension, the at least one elongate element is arranged to extend on the first side of the outer surface of the hinge, and when the orthopedic device is in flexion the at least one elongate element is arranged to progress from the first side of the hinge to the second side by crossing the instantaneous center of rotation at a predetermined flexion angle.

2. The orthopedic device of claim 1, wherein the upper frame includes first and second upper struts on opposed sides of the orthopedic device generally along the coronal plane and supporting a posterior portion of the upper frame adapted to secure about a posterior leg.

3. The orthopedic device of claim 2, wherein the dynamic loading component is arranged to extend on a posterior side of a leg between the first and second upper struts.

4. The orthopedic device of claim 2, wherein the first and second upper struts each define a cutout arranged in the sagittal plane and directed toward the dynamic loading component.

5. The orthopedic device of claim 1, further comprising a load adjuster located on a hinge cover defining the outer surface of the hinge for adjusting a load exerted by the dynamic loading component, the load adjuster being formed by a thickened region along the coronal plane of the hinge cover.

6. The orthopedic device of claim 1, further comprising an anti-migration strap located between the hinge and the lower frame, the anti-migration strap arranged to counteract the first load exerted by the dynamic loading component.

7. The orthopedic device of claim 1, wherein the upper cable guide defines a channel arranged along the sagittal plane and extending to the outlet.

8. The orthopedic device of claim 1, wherein the upper cable guide defines a channel arranged between the inlet and the outlet.

9. The orthopedic device of claim 1, wherein the at least one elongate element extends from a lower cable guide connected to the lower frame, the at least one elongate element extending between the upper and lower cable guides and over the hinge, the at least one elongate element having a movement profile forming a V-shape with the crest of the V-shape anchored to the lower cable guide.

* * * * *